United States Patent [19]

Braxton

[11] Patent Number: 5,766,897
[45] Date of Patent: Jun. 16, 1998

[54] CYSTEINE-PEGYLATED PROTEINS

[75] Inventor: Scott M. Braxton, San Mateo, Calif.

[73] Assignee: Incyte Pharmaceuticals, Inc., Palo Alto, Calif.

[21] Appl. No.: 427,100

[22] Filed: Apr. 21, 1995

Related U.S. Application Data

[63] Continuation-in-part of PCT/US94/11624 Oct. 28, 1994, continuation-in-part of Ser. No. 144,758, Oct. 29, 1993, abandoned, which is a continuation-in-part of Ser. No. 924,294, Aug. 3, 1992, Pat. No. 5,457,090, which is a continuation of Ser. No. 542,484, Jun. 21, 1990, Pat. No. 5,187,089.

[51] Int. Cl.⁶ .............. C12N 15/00; C12N 9/96; C12N 9/48; C12N 9/50
[52] U.S. Cl. .............. 435/172.1; 435/188; 435/212; 435/219
[58] Field of Search .............. 514/12; 530/350; 435/69.2, 188, 172.1, 212, 219

[56] References Cited

U.S. PATENT DOCUMENTS

| | | | |
|---|---|---|---|
| 4,179,337 | 12/1979 | Davis et al. | 435/181 |
| 4,474,752 | 10/1984 | Haslam et al. | 424/78 |
| 4,478,822 | 10/1984 | Haslam et al. | 424/78 |
| 4,657,760 | 4/1987 | Kung et al. | 424/85 |
| 4,690,915 | 9/1987 | Rosenberg | 514/2 |
| 4,731,439 | 3/1988 | Marquardt et al. | 530/324 |
| 4,766,106 | 8/1988 | Katre et al. | 514/12 |
| 4,816,439 | 3/1989 | Jorgensen | 514/12 |
| 4,863,910 | 9/1989 | Takayanagi | 514/150 |
| 4,902,502 | 2/1990 | Nitecki et al. | 424/83 |
| 4,965,251 | 10/1990 | Stamatoyannopoulos | 514/8 |
| 4,978,332 | 12/1990 | Luck et al. | 604/19 |
| 5,006,509 | 4/1991 | Waago | 514/12 |
| 5,010,175 | 4/1991 | Rutter et al. | 530/334 |
| 5,013,718 | 5/1991 | Adamson et al. | 514/8 |
| 5,032,574 | 7/1991 | Wilde et al. | 514/12 |
| 5,089,261 | 2/1992 | Nitecki et al. | 424/85 |
| 5,089,274 | 2/1992 | Marra et al. | 424/534 |
| 5,112,608 | 5/1992 | Scott et al. | 424/94.64 |
| 5,122,614 | 6/1992 | Zalipsky | 548/520 |
| 5,140,008 | 8/1992 | Jorgensen | 514/12 |
| 5,166,322 | 11/1992 | Shaw et al. | 530/351 |
| 5,182,259 | 1/1993 | Kita | 514/8 |
| 5,187,089 | 2/1993 | Scott et al. | 435/212 |
| 5,196,196 | 3/1993 | Scott et al. | 424/94 |
| 5,198,417 | 3/1993 | Donahue | 514/2 |
| 5,206,344 | 4/1993 | Katre et al. | 530/351 |
| 5,223,409 | 6/1993 | Ladner et al. | 435/69.7 |
| 5,225,212 | 7/1993 | Martin et al. | 424/450 |
| 5,234,903 | 8/1993 | Nho et al. | 514/6 |
| 5,234,912 | 8/1993 | Marra et al. | 514/21 |
| 5,260,066 | 11/1993 | Wood et al. | 424/447 |
| 5,264,209 | 11/1993 | Mikayama et al. | 424/85.2 |
| 5,283,317 | 2/1994 | Saifer et al. | 528/405 |
| 5,290,773 | 3/1994 | Takayanagi | 514/184 |
| 5,292,724 | 3/1994 | Kita | 514/21 |
| 5,298,410 | 3/1994 | Phillips et al. | 435/188 |
| 5,326,562 | 7/1994 | Scott | 424/94.64 |
| 5,348,942 | 9/1994 | Little, II et al. | 514/22 |
| 5,354,934 | 10/1994 | Pitt et al. | 514/8 |

US005766897A

FOREIGN PATENT DOCUMENTS

| | | |
|---|---|---|
| 0 251 505 | 1/1988 | European Pat. Off. |
| 0 584 876 A2 | 3/1994 | European Pat. Off. |
| WO 91/19787 | 12/1991 | WIPO |
| WO 92/20371 | 11/1992 | WIPO |
| WO 93/00109 | 1/1993 | WIPO |
| WO 93/15189 | 8/1993 | WIPO |
| WO 93/16118 | 8/1993 | WIPO |

OTHER PUBLICATIONS

Lehninger, A.L., "The molecular basis of cell structure and function," Biochemistry, Second Edition, Worth Publishers, Inc., (1975) pp. 72–75.

Dellinger, C.T., "Comparison of anaphylactic reactions to asparaginase derived from Escherichia Coli and from Erwinia cultures," (1976) Cancer 38(4):1843–1846.

Savoca et al., "Preparation of a non–immunogenic arginase by the covalent attachment of polyethylene glycol," Biochimica et Biophysica ACTA, (1979) 578:47–53.

Bieth, J.G., "Pathophysiological interpretation of kinetic constants of protease inhibitors," Bull. Euro. Physiopath. Resp. (1980) 16:183–195.

Davis et al., "Hypouricaemic effect of polyethyleneglycol modified urate oxidase," (1981) Lancet 2:281–283.

Davis, S. et al., "Alteration of the circulating life and antigenic properties of bovine adenosine deaminase in mice by attachment of polyethylene glycol," (1981) Clin. exp. Immunol. 46:649–652.

Knauer, D.J. et al., "The γ subunit of 7 S nerve growth factor binds to cells via complexes formed with two cell–secreted nexins," (1982) J. Biol. Chem. 257(23):15098–15104.

Veronese, et al., "Anti–inflammatory and pharmacokinetic properties of superoxide dismutase derivatized with polyethylne glycol via active esters," (1983) J. Pharm. Pharmacol. 35:281–283.

(List continued on next page.)

Primary Examiner—Keith D. Hendricks
Assistant Examiner—Lisa J. Hobbs
Attorney, Agent, or Firm—Fish & Richardson P.C.

[57] ABSTRACT

Methods and compositions are provided for the production of PEGylated proteins having polyethylene glycol covalently bound to a cysteine residue present in either the naturally-occurring protein or introduced by site-specific mutation. Where the cysteine residue is introduced by mutation, the site for mutation is selected on the basis of the presence of an N-linked glycosylation site or the position of the residue which is normally solvent-accessible in the naturally-occurring protein. The modified proteins produced by the method of the invention are referred to as cysteine-PEGylated proteins. Proteins PEGylated according to the invention have increased half-lives following administration to a subject and decreased immunogenicity and antigenicity, while retaining substantially the same level of biological activity as that of the naturally-occurring, unmodified protein. Modification of proteins according to methods of the invention thus provide improved pharmaceutical compositions.

10 Claims, 7 Drawing Sheets

OTHER PUBLICATIONS

Eaton, D.L. et al., "Purification of human fibroblast urokinase proenzyme and analysis of its regulation by proteases and protease nexin," (1984) *J. Biol. Chem.* 259(10):6241–6247.

Travis, J. et al., "Human plasma proteinase inhibitors," (1983) *Ann. Rev. Biochem.* 52:655–709.

Eaton, D.L. et al., "Phorbol ester and mitogens stimulate human fibroblast secretions of plasmin–activatable plasminogen activator and protease nexin, an antiactivator/antiplasmin," (1983) *J. Cell Biol.* 97(2):323–8.

Till, G.O. et al., "Oxygen radical dependent lung damage following thermal injury of rat skin," (1983) *J. Trauma* 23(4):269–277.

Scott, R.W. et al., "Purification of human protease nexin," (1983) *J. Biol. Chemistry* 258(7):10439–10444.

Nishimura, H. et al., "Modification of batroxobin with activated polyethylene glycol: reduction of binding ability towards anti–batroxobin antibody and retention of defrinogenation activity in circulation of preimmunized dogs," (1983) *Life Sciences* 33:1467–1473.

Scott, R.W., et al., "Protease–nexin," (1985) *J. Biol. Chem.* 260(11):7029–7034.

Courtney, M., et al., "Synthesis in *E. coli* of $\alpha_1$–antitrypsin variants of therapeutic potential for emphysema and thrombosis," (1985) *Nature* 313:149–151.

Gardell et al., "Site–directed mutagenesis shows that tyrosine 248 of carboxypeptidase A does not play a crucial role in catalysis," (1985) *Nature* 317:551–555.

Graf, L., et al., "Selective alteration of substrate specificity by replacement of aspartic acid–189 with lysine in the binding pocket of tryspin," (1987) *Biochemistry* 26:2616–2623.

Farrell, D.H., et al. "Glycosaminoglycans on fibroblasts accelerate thrombin inhibition by protease nexin–1," (1987) *Biochem. J.* 245:543–550.

Baker, J.B., et al., "Protease nexin I. Structure and potential functions," (1987) *The Pharmacology and Toxicology of Proteins, UCLA Symposia*, Alan R. Liss, Inc., Series V, 65:307–323.

Sommer, J. et al., "cDNA sequence coding for a rat gli–derived nexin and its homology to members of the serpin superfamily," (1987) *Biochemistry* 26:6407–6410.

McGrogan, M. et al., "Molecular cloning and expression of two forms of human protease nexin I," (1988) *Bio/Technology* 6:172–177.

Cunningham B.C. et al. "High–resolution epitope mapping of hGH–receptor interactions by alanine–scanning mutagenesis," (1989) *Science* 244:1081–1085.

Engh, R.A., et al., "Modeling the intact form of the $\alpha_1$–proteinase inhibitor," (1990) *Protein Engineering* 3(5):469–477.

Nucci, M.L. et al., "The therapeutic value of poly(ethylene glycol)–modified proteins," (1991) *Adv. Drug Delivery Res.* 6:133–151.

Evans, D.L., "Protease specificity and heparin binding and activation of recombinant protease nexin I," (1991) *J. Biol. Chem.* 266(33):22307–22312.

De Vos, A.M. et al., "Human growth hormone and extracellular domain of its receptor: crystal structure of the complex," (1992) *Science* 255:306–312.

Hedstrom, L. et al., "Converting trypsin to chymotrypsin: the role of surface loops," (1992) *Science* 255:1249–1253.

Konrad, M.W., "The immune system as a barrier to delivery of protein therapeutics," (1993) *Biological Barriers to Protein Delivery*, Plenum Press, N.Y. and London, Chapter 14, pp. 409–437.

Ferraiolo, B.L. et al., "Goals and analytical methodologies for protein disposition studies," (1992) *Protein Pharmacokinetics and Metabolism*, Plenum Press, NY, Chapter 1, pp. 1–33.

SEQUENCE OF PROTEASE NEXIN I TYPE ALPHA

FIG. 1A

```
CCG CTG TCT GCC ATC CCA CAC ATC AGC ACC AAG ATA GAC AGC ATC ATG GTG CCC AAG AGG GTG CAG GTG ATC CTG
Pro Leu Ser Ala Ile Pro His Ile Ser Thr Lys Ile Asp Ser Ile Met Val Pro Lys Arg Val Gln Val Ile Leu
         250                              260                              270
CCC AAG TTC ACA GCT GTA GCA CAA GAT TTG AAG GAG CCG CTG AAA GTT CTT GGC ATT ACT GAC ATG TTT GAT TCA AAG GCA AAT
Pro Lys Phe Thr Ala Val Ala Gln Asp Leu Lys Glu Pro Leu Lys Val Leu Gly Ile Thr Asp Met Phe Asp Ser Lys Ala Asn
    280                              290                              300
                                                                                                HindIII
TTT GCA AAA ATA ACA AGG TCA GAA AAC CTC CAT GTT TCT CAT ATC TTG CAA AAA GCA AAA ATT GAA GTC AGT GAA GAT GGA ACC AAA GCT
Phe Ala Lys Ile Thr Arg Ser Glu Asn Leu His Val Ser His Ile Leu Gln Lys Ala Lys Ile Glu Val Ser Glu Asp Gly Thr Lys Ala
         310                              320                              330
                                   345 346
TCA GCA GCA ACA ACT GCA ATT CTC ATT GCA AGA TCA TCG CCT CCC TGG TTT ATA GTA GAC AGA CCT TTT CTG TTT TTC ATC CGA CAT AAT
Ser Ala Ala Thr Ala Ile Leu Ile Ala Arg Ser Ser Pro Pro Trp Phe Ile Val Asp Arg Pro Phe Leu Phe Phe Ile Arg His Asn
    340                              350                              360
                      378
CCT ACA-GGT GCT GTG TTA TTC ATG GGG CAG ATA AAC AAA CCC TGA AGAGTATACAAAAGAACAACGTAGTTCTTCAAAACGTAGTTCTTAGGAAGCAGACTGATGCAACGTGTTCCTGTTCTGGGAGGTATTGGAGGGAAAAAACA
Pro Thr Gly Ala Val Leu Phe Met Gly Gln Ile Asn Lys Pro ---
         370
AGCAGGATGCCTAGGAATTGTTCCTTTAAATTCTTTCCCCATCCCCTCCCAAAGTCTTGATAGCAAGGTTATTTTGGGGTAGAAACGGTGAAATCTCTAGCCTCTTTGTGTTTTGTTGTT
GTTGTCCAGTAGGAATTAGTTCCTTAAATGCATGTTTTATATATGCATGTATTCATAAATAAAATTTAAAAAAACGTCCGTCTTGCTAGACAAGGTTGCATGTGCCTGTCACTACTGAGTCTGTCTACCTATGGA
AAAAATTATTTGTTGTTGTTTTGTACAAGTAAAAAATAACT
GTTGTTGTTGTTTATATGCATGTATTTTGTACAAGTAAAAAATAACT
TTGCATTTTGTATTTGTACAAGTAAAAAATAACT
```

FIG. 1B

SEQUENCE OF PROTEASE NEXIN I TYPE BETA

```
CTGTGACCCTCCTCGCCGCCGCCTTGCTGCTCGACTCCCGCCGCCGAGACTAGGCTCCGTCCGGGCACCCCCTCCGGCGCGCCCCTGGGGATCCAGCGAGCG

S10                                          1
CGGTCGTCCTTGGTGGAAGGAACC ATG AAC TGG CAT CTC CCC CTC TTC GCC TTG CTC CCT GTG ACG CTG CCT TCC ATC TGC CAC TTC AAT
                         Met Asn Trp His Leu Pro Leu Phe Ala Leu Leu Pro Val Thr Leu Pro Ser Ile Cys His Phe Asn
                                                         10                                         20                                         30
CCT CTG TCT CTC GAG GAA CTA GGC TCC AAC ACG GGG ATC CAG GTT TTC AAT CAG ATT GTG AAG TCG AGG CCT CAT GAC AAC ATC GTG ATC
Pro Leu Ser Leu Glu Glu Leu Gly Ser Asn Thr Gly Ile Gln Val Phe Asn Gln Ile Val Lys Ser Arg Pro His Asp Asn Ile Val Ile
                      40                                         50                                         60
TCT CCC CAT GGG ATT GCG TCG GTC CTG GGG ATG CTT CAG CTG GGG GAC GCG AGG ACC AAG CAG CTC GCC ATG GTG ATG AGA TAC
Ser Pro His Gly Ile Ala Ser Val Leu Gly Met Leu Gln Leu Gly Asp Ala Asp Gly Ala Arg Thr Lys Lys Gln Leu Ala Met Val Met Arg Tyr
                      70                                         80                                         90
GGC GTA AAT GGA GTT GGT AAA ATA TTA AAG AAG ATC AAC AAG GCC ATC GTC TCC AAG AAG AAT AAA GAC ATT GTG ACA GTG GCT AAC GCC
Gly Val Asn Gly Val Gly Lys Ile Leu Lys Lys Ile Asn Lys Ala Ile Val Ser Lys Lys Asn Lys Asp Ile Val Thr Val Ala Asn Ala
                      100                                        110                                        120
GTG TTT GTT AAG AAT GCC TCT GAA ATT GAA GTG CCT TTT GTT ACA AGG GAT GTG TTC CAG TGT GAG GTC AAT GTG AAC TTT
Val Phe Val Lys Asn Ala Ser Glu Ile Glu Val Pro Phe Val Thr Arg Asp Val Phe Gln Cys Glu Val Arg Asn Val Asn Phe
                      130                                        140                                        150
GAG GAT CCA GCC TCT GCC TGT GAT TCC ATC AAT GCA TGG GTT AAA ACC GAA AAT GAA AGG GAT ATT GAC AAT CTG TCC CCA GAT CTT
Glu Asp Pro Ala Ser Ala Cys Asp Ser Ile Asn Ala Trp Val Lys Thr Glu Asn Glu Arg Asp Met Ile Asp Asn Leu Ser Pro Asp Leu
                      160                                        170                                        180
ATT GAT GTG GTG CTC ACC AGA CTG GTG CTC GTC AAC GCA GTG TAT TTC AAG GGT CTG TGG AAA TCA CGG TTC TCC GAG AAC ACA AAG
Ile Asp Val Val Leu Thr Arg Leu Val Leu Val Asn Ala Val Tyr Phe Lys Gly Leu Trp Lys Ser Arg Phe Ser Glu Asn Thr Lys
                      190                                        200                                        210
AAA CGC ACT TTC GTG GCA GCC GAC GGG AAA TCC TAT CAA GTG CCA ATG ATG TCG CAG CTC GTG TTC CGG TGT GGG GTA ACA AGT GCC
Lys Arg Thr Phe Val Ala Ala Asp Gly Lys Ser Tyr Gln Val Pro Met Met Ser Gln Leu Val Phe Arg Cys Gly Thr Ser Ala
                      220                                        230                                        240
CCC AAT GAT TTA TGG TAC AAC TTC GAA CTG CCT TAC CAC CCC GAA AGC ATC AGC ATG CTG ATT GCA CTG CCG ACA AGT TCC ACT
Pro Asn Asp Leu Trp Tyr Asn Phe Glu Leu Pro Tyr His Pro Glu Ser Ile Ser Met Leu Ile Ala Leu Pro Thr Ser Ser Thr
```

FIG. 2A

```
                                           250                                          260
CCG CTG TCT GCC ATC ATC CCA CAC ATC AGC ACC AAG ACC ATA GAC TGG ATG AGC ATC ATG GTG CCC AAG AGG CAG GTG ATC CTG
Pro Leu Ser Ala Ile Ile Pro His Ile Ser Thr Lys Thr Ile Asp Trp Met Ser Ile Met Val Pro Lys Arg Gln Val Ile Leu
                  270                                          280                                          290
CCC AAG TTC ACA GCT GTA GCA CAA ACA GAT TTG AAG GAG CCG CTG AAA GTT CTT GGC ATT ACT GAC ATG TTT GAT TCA AAG GCA AAT
Pro Lys Phe Thr Ala Val Ala Gln Thr Asp Leu Lys Glu Pro Leu Lys Val Leu Gly Ile Thr Asp Met Phe Asp Ser Lys Ala Asn
                          300                                          310                                          Hind III
TTT GCA AAA ATA ACA ACA GGG TCA GAA AAC CTC CAT GTT TCT CAT GTT TCA GAA ATT GAA GTC AAA GCA AAA ATT GAA GTC AAA GCA GAT GGA ACC AAA
Phe Ala Lys Ile Thr Thr Gly Ser Glu Asn Leu His Val Ser His Val Ser Glu Ile Glu Val Ser Glu Ile Glu Val Lys Ala Lys Asp Gly Thr Lys
                                  320                                          330
                                  346 347
GCT TCA GCA ACA ACT GCA ATT CTC ATT GCA ATA TCA GAA ATC GCC TGG TTT ATA GTA GAC AGA CCT TTT CTG TTT TTC ATC CGA CAT
Ala Ser Ala Thr Thr Ala Ile Leu Ile Ala Ile Ser Glu Ile Ala Trp Phe Ile Val Asp Arg Pro Phe Leu Phe Phe Ile Arg His
                                          350                                          360
AAT CCT ACA GGT GCT GTG TTA TTC ATG GGG CAG ATA AAC CCC TGA AGAGTATACAAAGAAGAACCATGCAAAGCAACGACTACTTTGCTACGAAGAAGACT
Asn Pro Thr Gly Ala Val Leu Phe Met Gly Gln Ile Asn Lys Pro ---
                                  370       378

CCTTCCTGCATCTTCTTGTTAAATATTCTGTACATCGCATTCTTTTCAAAACGTAGTTCTTAGGAAGCAGACTCGATGCAACTGTTCCTGTTCTGGGAGGTATTGGAGGAAAA
ACAAGCAGGATGCCTGGCACAGTGCTACTGAGGATTGATATAGAAAGACTTCCAGATGCCTAAAAAGATTCTTAACTACTGAACTGTTACCTAGTTAACATCCTGTTGAGGTATTT
GCTGTTGTCCAGTAGGAATTTTGTTTGTTTGTCTCTATATGTGCCCCTCCCATCCCCCTCCAAAGTCTGATAGCAAGGGTTATTTGGGGGGTAGAAACGGTGAAATCTCTAGCCTCTTGTGTTTGTT
AAAAAAATTATTGTCCTTTAAATTCTTTTCCCATCCTAAAATAAAATTTAAAAAACGTCCTGTCTTGCTAGACACAAGGTTGCATGCCTGTCACTACTGAGTCTGCTCTACCTAT
GTTGTTGTTGTTTATATAATGCATGTATTCACTAAATAAATGCATGTATTCACTAAATAAATTTAAAAAACGTCCTGTCTTGCTAGACAAGTAAAAATAACT
GGATTTGCATTTTTGTATTTTGTACAAGTAAAAATAACT
```

CYSTEINE-PEGYLATED PROTEINS

CROSS REFERENCE TO RELATED APPLICATIONS

This application is a continuation-in-part of our earlier filed application, PCT application Ser. No. PCT/US94/11624, filed Oct. 28, 1994, which is a continuation-in-part of U.S. application Ser. No. 08/144,758, filed Oct. 29, 1993, now abandoned, which is a continuation-in-part of application Ser. No. 07/924,294, filed Aug. 3, 1992, which issued as U.S. Pat. No. 5,457,090, which is a continuation of application Ser. No. 07/542,484, filed Jun. 21, 1990 which issued as U.S. Pat. No. 5,187,089 on Feb. 16, 1993 to which applications we claim priority under 35 USC § 120 and § 365(c) which applications are incorporated herein by reference in their entirety.

FIELD OF THE INVENTION

This invention relates to identifying cysteine residues, or amino acid residues which may be substituted by cysteine, and attaching polyethylene glycol to the thio group of cysteine, thereby increasing protein stability without abolishing biological activity.

BACKGROUND OF THE INVENTION

The value of biologically active proteins in therapy has been long recognized in the art. Proteins are ideal as therapeutics due to their specificity of action, their effectiveness in vivo at relatively low concentrations, and their rapid catalytic action. Numerous proteins have been isolated and developed for use in, for example, treatment of conditions associated with a protein deficiency (e.g., human growth hormone, insulin); enhancement of the immune response (e.g., antibodies, cytokines); treatment of cancer (e.g., cytokines, L-asparaginase, superoxide dismutase, monoclonal antibodies); treatment of conditions associated with excessive or inappropriate enzymatic activity (e.g., inhibition of elastase with α1-antitrypsin, regulation of blood clotting with antithrombin-III); blood replacement therapy (e.g., hemoglobin); treatment of endotoxic shock (e.g., bactericidal-permeability increasing (BPI) protein); and wound healing (e.g., growth factors, erythropoietin). The foregoing examples are only representative of the vast possibilities in the field of protein therapy.

Development of protein therapies is hampered by the relatively short half-life of proteins after administration, as well as their immunogenicity. Most proteins, particularly relatively low molecular weight proteins introduced into the circulation, are cleared quickly from the mammalian subject by the kidneys. This problem may be partially overcome by administering a larger amount of the protein or through repeated administration. However, higher doses of the protein can elicit antibodies which can bind and inactivate the protein and/or facilitate the clearance of the protein from the subject's body. Repeated administration of the therapeutic protein is essentially ineffective and can be dangerous as it can elicit an allergic response.

Various attempts to solve the problems associated with protein therapies include microencapsulation, liposome delivery systems, administration of fusion proteins, and chemical modification. The most promising of these to date is modification of the therapeutic protein by covalent attachment of polyalkylene oxide polymers, particularly polyethylene glycols (PEG). For example, U.S. Pat. No. 4,179,337 discloses the use of PEG or polypropylene glycol coupled to proteins to provide a physiologically active non-immunogenic water soluble polypeptide composition. Nucci et al. describe several proteins which have been modified by addition of PEG including adenosine deamidase, L-asparaginase, interferon alpha 2b (IFN-α2b), superoxide dismutase, streptokinase, tissue plasminogen activator (tPA), urokinase, uricase, hemoglobin, interleukins, interferons, TGF-β, EGF, and other growth factors (Nucci et al., 1991, *Adv. Drug Delivery Rev.* 4:133–151). Attempts such as these have resulted in somewhat longer half-life of the proteins and reduction of protein immunogenicity.

Typically, PEGylation of proteins involves activating PEG with a functional group which will react with lysine residues on the surface of the protein. If the modification of the protein goes to completion, the activity of the protein is usually lost. Modification procedures which allow partial PEGylation of the protein usually result in only about 50% loss of activity and greatly increased serum half-life, so that the overall effective dose of the protein is lower.

However, an unavoidable result of partial modification is the production of a heterogenous mixture of PEGylated protein having a statistical distribution of the number of PEG groups bound per protein. In addition, the usage of lysine residues within the protein is random. These two factors result in the production of a heterogeneous mixture of PEGylated proteins which differ in both the number and position of the PEG groups attached. For instance, when adenosine deaminase is optimally modified there is a loss of 50% activity when the protein has about 14 PEG per protein, with a broad distribution of the actual number of PEG moieties per individual protein and a broad distribution of the position of the actual lysine residues used. Such mixtures of diversely modified proteins are not suitable as pharmaceutical compositions. Purification and isolation of a class of PEGylated proteins (e.g., proteins containing the same number of PEG moieties) or a single type of PEGylated protein (e.g., proteins containing both the same number of moieties and having the PEG moieties at the same position) involves time-consuming and expensive procedures which result in an overall reduction in the yield of the specific PEGylated protein of interest. This complication can render use of PEGylated proteins economically impractical.

In addition to problems associated with loss of activity and production of heterogenous mixtures of partially modified proteins, conventional lysine-PEGylation protocols are also disadvantageous in their use of toxic reagents during the PEGylation reaction. For example, early methods for PEG modification activated PEG by reaction with cyanuric chloride, a highly toxic chemical. The presence of such toxic reagents poses a serious technical difficulty in the preparation of a pharmaceutical compositions for administration, and may require numerous additional steps to ensure the purity of the final pharmaceutical preparation.

Recent, significant advances have reduced the need for highly toxic chemicals in the PEGylation reactions. For example, Zalipsky et al. (1991 *Polymeric Drugs and Drug Delivery Systems* ACS.) describe the use of succinimydyl carbonates of PEG to produce stable carbamate linkages with proteins via free lysine residues. There are several other methods for modification of proteins with PEG through free lysine residues, but each suffers from the problems associated with partial, random modification of protein and the potential for losing activity if lysine residues are essential for biological activity.

An alternative approach is to PEGylate other residues such as His, Trp, Cys, Asp, Glu, etc. without loss of activity.

Many of these residues are not acceptable candidates for PEGylation as they are likely to be at or near the active site, or will not be at the surface of the protein and thus will be inaccessible for modification. Moreover, these residues are not likely to be present in the protein in sufficient numbers to significantly affect serum half-life. Furthermore, the modification chemistry is likely not specific enough for the target residue and/or is too harsh and will result in loss of protein activity.

More recent developments in protein PEGylation methods employ activated PEG reagents which react with thio groups of the protein, resulting in covalent attachment of PEG to a cysteine residue, which residue was inserted in place of a natrually-occuring lysine residue of the protein. Shaw et al. (U.S. Pat. No. 5,166,322) describe specific variants of IL-3 which have a cysteine residue introduced at specific sites within the naturally occurring amino acid sequence. Sulfhydryl reactive compounds (e.g. activated polyethylene glycol) are then attached to these cysteines by reaction with the IL-3 variant. Katre et al. (U.S. Pat. No. 5,206,344) describe specific IL-2 variants which contain a cysteine residue introduced at a specific site within the naturally-occurring amino acid sequence. The IL-2 variant is subsequently reacted with an activated polyethylene glycol reagent to attach this moiety to a cysteine residue.

There is a clear need for a method for generating PEGylated proteins for therapeutic use which does not require knowledge of the amino acid residues essential for biological activity. There is also need for a method of generating PEGylated proteins which uses no or fewer toxic chemicals and which is highly specific for modification of pre-selected amino acid residues for PEGylation. Such PEGylation methods would increase the likelihood of generation of homogeneously PEGylated proteins which retain the activity of the unmodified parent protein.

SUMMARY OF THE INVENTION

PEGylated proteins are produced wherein a cysteine residue, which is either present in the native protein or introduced by site-specific mutation, is used to attach a polyethylene glycol moiety. The proteins of the invention having polyethylene glycol covalently attached to a thio group, normally a thio group of a cysteine residue, are referred to herein as cysteine-PEGylated proteins.

Still another important object is to provide proteins which are PEGylated by attachment to a thio group, i.e. the polyethylene glycol is attached to a cysteine amino acid within a protein, which cysteine amino acid of the protein is not involved in a disulfide bond.

Another important object is to provide a method of attaching polyethylene glycol to a protein by first subjecting the protein to site-directed mutagenesis to add a cysteine residue at a position where the protein or a structurally related protein is normally glycosylated, and thereafter attaching the polyethylene glycol to the cysteine residue.

Another important object is to provide a method of attaching PEG to a protein by first subjecting the protein to site-directed mutagenesis to add a cysteine residue at a position on the surface of the protein, and thereafter attaching the PEG to the cysteine residue.

Another important object is to provide dimeric or multimeric proteins cross-linked by reaction with a reagent composed of PEG having two protein-reactive moieties.

Another object of the present invention is to provide a pharmaceutical composition comprising excipient carrier materials having a compound of the invention dispersed therein.

Another object of the present invention is to provide therapeutic methods of treatment which involve administering to a patient in need thereof a pharmaceutically effective amount of a composition comprising excipients and a compound of the invention.

Yet another object is to provide methods of delivery such as by injection, intranasal and intrapulmonary delivery which methods are carried out using pharmaceutical compositions in the form of injectable formulations, spray formulations and aerosols.

Another advantage is that biologically stabilized proteins can be produced by attaching the polyethylene glycol to a cysteine residue of the protein.

Another advantage is to provide methodology for readily attaching polyethylene glycol molecules to proteins at a cysteine residue of the protein which are preferably located at native sites of glycosylation.

Yet another advantage is that amino acid residues for substitution with cysteine may be selected so that subsequent attachment of polyethylene glycol to the thio group of the substituted cysteine residue increases biological stability of the cysteine-PEGylated protein relative to wild type without abolishing biological activity.

Another advantage is that proteins which normally require glycosylation for biological stability may be produced commercially by expression in a prokaryotic host or other host which does not provide for glycosylated recombinant proteins. After expression of the protein by the prokaryotic host, biological stability of the protein can be increased by attachment of polyethylene glycol to a native or engineered cysteine residue in the protein.

Another advantage is that cysteine-PEGylated proteins can be produced without exposing the protein to highly toxic chemicals such as dioxane, cyanuric chloride, DMF, or other chemicals used in conventional methods for attaching polyethylene glycol to a protein.

These and other objects, advantages and features of the present invention will become apparent to those persons skilled in the art upon reading the details of the structure, synthesis, formulation and usage as more fully set forth below reference being made to the accompany figures forming a part hereof.

BRIEF DESCRIPTION OF THE DRAWINGS

FIGS. 1A and 1B show the nucleotide sequence of the coding region and the deduced amino acid sequence of PN-1α; and FIGS. 2A and 2B show the nucleotide sequence of the coding region and the deduced amino acid sequence of PN-1β.

DETAILED DESCRIPTION OF THE PREFERRED EMBODIMENT

Figure 3:
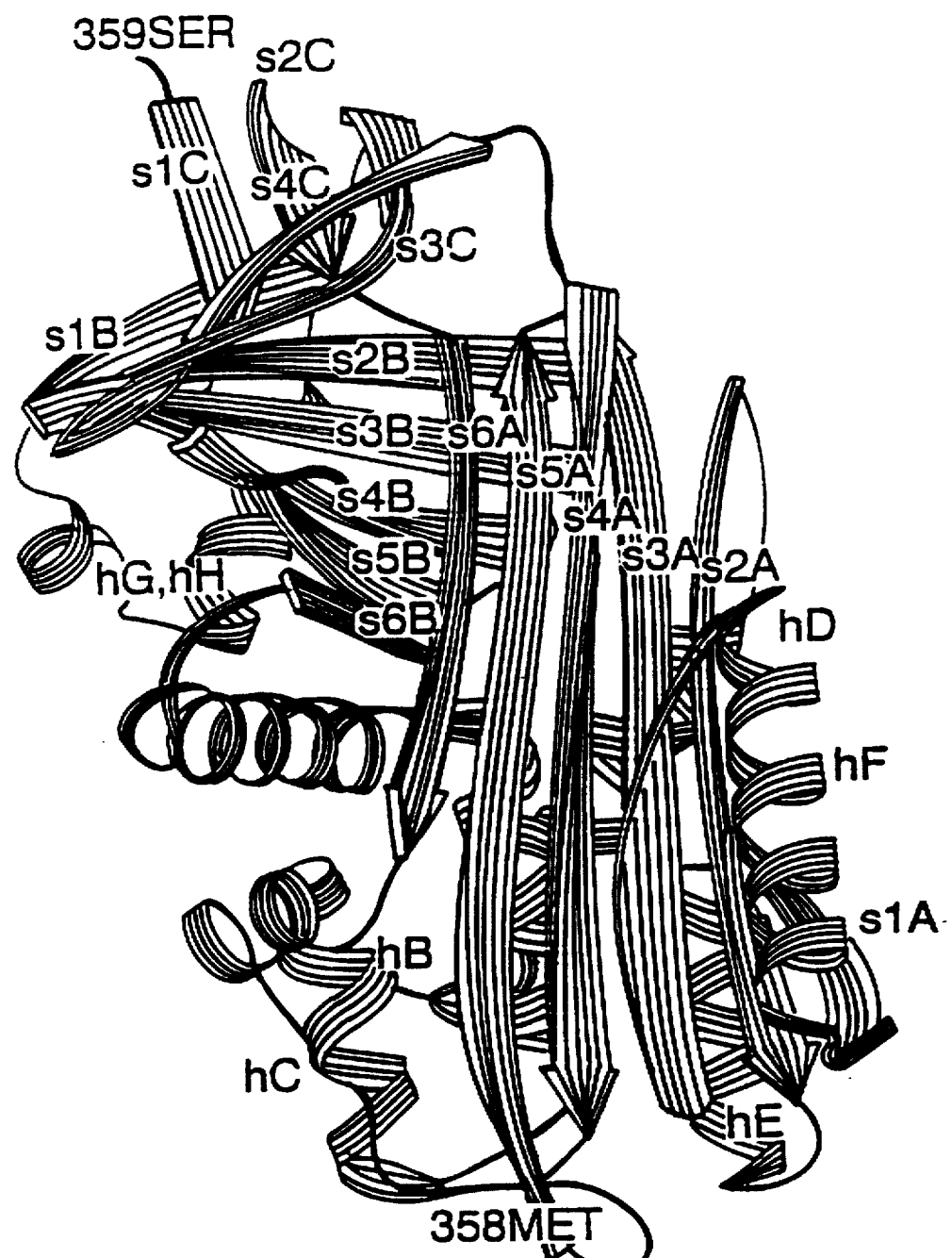
FIG. 3 is a schematic drawing of a three-dimensional structure of PN-1 as determined by X-ray crystallography. The approximate position of residues of particular interest are shown according to their relative position within a given helix (h) or β-sheet (s). The helices and β-sheets of the PN-1 protein are each assigned letters (e.g. A, B, etc.) (Engh, et al. 1990 *Protein Engin.* 3(6) :469–477).

Before the present compounds, variants, formulations and methods for making and using such are described, it is to be understood that this invention is not limited to the particular compounds, variants, formulations or methods described, as such variants, formulations and methodologies may, of course, vary. It is to be understood that the terminology used herein is for the purpose of describing particular embodiments only, and is not intended to be limiting since the scope of the present invention will be limited only by the appended claims.

It must be noted that as used in the specification and the appended claims, the singular forms "a", "an" and "the" include plural referents unless the context clearly dictates otherwise. Thus, for example, reference to "a protease nexin-1 variant" includes mixtures of such variants, reference to "an analog" includes reference to mixtures of such analogs and reference to "the method of treatment" includes reference to one or more methods of treatment of the type which will be known to those skilled in the art or will become known to them upon reading this specification, and so forth.

A. Definitions

By "chemically modified protein" is meant a two part compound which has biological activity and which when administered to a mammal provides a therapeutic effect. The two parts include (1) a protein or a biologically active fragment thereof and (2) a chemical moiety (not naturally connected to the protein) covalently bound to the protein at a cysteine residue of the protein, wherein the chemical moiety is preferably polyethylene glycol (PEG).

By "PEGylated protein" is meant a protein, or a fragment thereof having biological activity, having a polyethylene glycol (PEG) moiety covalently bound to an amino acid residue of the protein.

By "cysteine-PEGylated protein" is meant a protein having a polyethylene glycol (PEG) moiety covalently bound via a thio group of a cysteine residue present in the protein.

By "polyethylene glycol" or "PEG" is meant a polyalkylene glycol compound or a derivative thereof, with or without coupling agents or derviatization with coupling or activating moeities (e.g., with thiol, triflate, tresylate, azirdine, oxirane, or preferably with a maleimide moiety). Compounds such as maleimido monomethoxy PEG are exemplary or activated PEG compounds of the invention. Other polyalkylene glycol compounds, such as polypropylene glycol, may be used in the present invention. Other appropriate polyalkylene glycol compounds include, but are not limited to, charged or neutral polymers of the following types: dextran, colominic acids or other carbohydrate based polymers, polymers of amino acids, and biotin deriviatives.

Figure 1A:
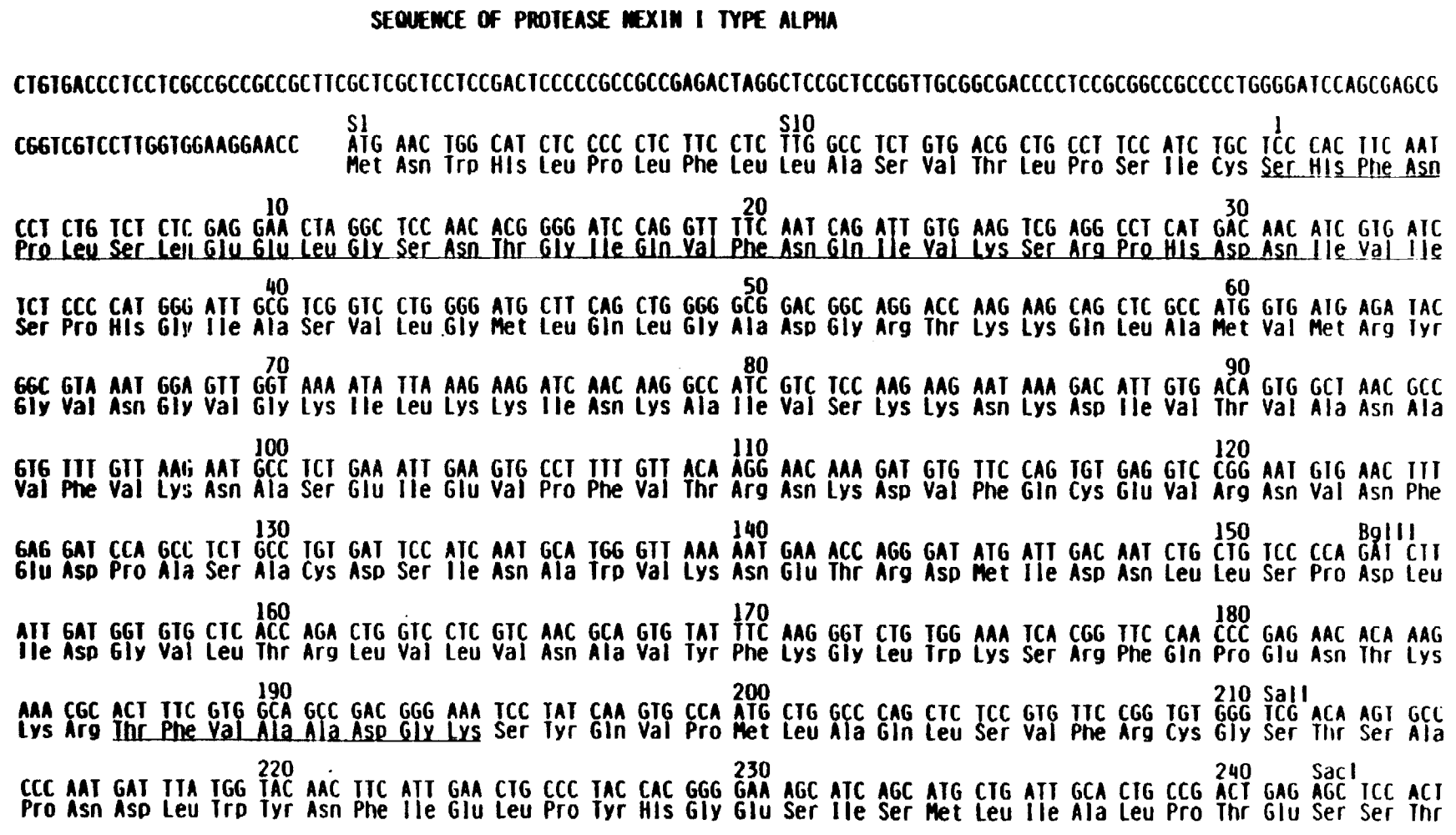

As used herein, "protease nexin-1" and "PN-1" are used interchangeably and refer to DNA codons and resulting amino acid sequences which make up PN-1α and PN-1β which are shown respectively in FIGS. 1A to 1B and FIGS. 2A to 2B. PN-1 is distinguishable from the two other protease nexin factors, PN-II and PN-III (Knauer, D. J. et al., *J. Biol. Chem.* (1982) 257:15098-15104), which are also thrombin inhibitors, but are less strongly binding to this protease and are of different molecular weight, three-dimensional structure and mechanism of function.

The terms "variants", "protein variants" and "chimeric proteins" are used interchangeably herein to refer to any amino acid sequence which corresponds to the amino acid sequence of a natural protein or a biologically active portion of a natural protein except that some change has been made in the structures. Typical changes include: (1) one or more amino acids within the natural sequence is replaced with one or more amino acids different from the amino acids present in the natural protein; and/or (2) one or more amino acids has been added to the natural sequence, and the addition of such amino acids changes the biological activity of the variant; and/or (3) one or more amino acids is deleted from the natural sequence; and/or (4) two naturally occurring sequences are fused together, i.e. two natural sequences not naturally connected are covalently bound together.

"Protease nexin-1 variants" and "analogs of protease nexin-1" are terms which are used synonymously herein to define a variant of protease nexin-1 and are thereby encompassed by the term "variant." The terms are intended to refer generally to proteins wherein one or more of the amino acids within protease nexin-1 have been substituted with a different amino acid. More specifically, the protease nexin-1 variants of the invention include substantially the same amino acid sequence as protease nexin-1 but for the substitution of different amino acids at or near the active site. Specifically, substitutions of different amino acids can be made at any of $P_1$, $P_2$, $P_3$, $P_4$ sites and/or made at the $P_1'$, $P_2'$, $P_3'$, $P_4'$ sites. Although other substitutions and deletions of amino acids in the sequence of protease nexin-1 are encompassed by this invention, the substitutions at or near the active site are most important with respect to changing the specificity and/or reactivity of the variant with respect to particular proteases. Particularly preferred protease nexin-1 variants of the invention are variants which have high activity relative to a substrate to which natural PN-1 has little or no activity such as variants which inhibit elastase and, more particularly, which inhibit elastase and have their ability to inhibit elastase enhanced in the presence of heparin and/or heparin-like compounds. Other preferred protease nexin-1 variants, for example, have increased ability to inhibit urokinase and/or another serine protease as compared with protease nexin-1.

"Control sequence" refers to a DNA sequence or sequences which are capable, when properly ligated to a desired coding sequence, of effecting its expression in hosts compatible with such sequences. Such control sequences include at least promoters in both procaryotic and eucaryotic hosts, and preferably, transcription termination signals. Additional factors necessary or helpful in effecting expression may also be identified. As used herein, "control sequences" simply refers to whatever DNA sequence may be required to effect expression in the particular host used.

"Cells" or "cell cultures" or "recombinant host cells" or "host cells" are often used interchangeably as will be clear from the context. These terms include the immediate subject cell, and, of course, the progeny thereof. It is understood that not all progeny are exactly identical to the parental cell, due to chance mutations or differences in environment. However, such altered progeny are included in these terms, so long as the progeny retain the characteristics relevant to those conferred on the originally transformed cell. In the present case, for example, such a characteristic might be the ability to produce recombinant PN-1.

"Purified" or "pure" refers to material which is free from substances which normally accompany it as found in its native state. Thus "pure" PN-1-encoding DNA refers to DNA which is found in isolation from its native environment and free of association with DNAs encoding other proteins normally produced by cells natively producing PN-1. "Pure" PN-1 refers to PN-1 which does not contain materials normally associated with its in situ environment in human or other mammalian tissue. Of course, "pure" PN-1 may include materials in covalent association with it, such as glycoside residues or materials introduced for, for example, formulation as a therapeutic. The term "pure" also includes variants wherein compounds such as polyethylene glycol, Biotin or other moieties are bound to the variant in order to allow for the attachment of other compounds and/or provide for formulations useful in therapeutic treatment or diagnostic procedures. "Pure" simply designates a situation wherein the substance referred to is, or has been, isolated from its native environment and materials which normally accompany it. Of course, the DNA claimed herein as purified and free of substances normally accompanying it, but encoding PN-1, can include additional sequence at the 5' and/or 3' end of the coding sequence which might result, for example, from reverse transcription of the noncoding portions of the message when the DNA is derived from a cDNA library or might include the reverse transcript for the signal sequence as well as the mature protein encoding sequence.

By "completely free of" a recited compound is meant that the recited compound is not present at any level. For example, by a completely free of cyanuric chloride" is meant that no cyanuric chloride is present at any level.

By "highly toxic chemical" or "toxic chemical" is meant a compound which is deleterious to cells. The presence of such a compound in a pharmaceutical composition is highly undesirable, even when the highly toxic compound or toxic compound is present in minute quantities (e.g. parts per million or parts per billion). Exemplary toxic chemicals include cyanuric chloride, DMF, dioxane, and 1-hydroxy-2-nitrobenzene-4-sulfonic sodium salt (HNSA).

"Degenerate with", as referred to a DNA sequence, refers to nucleotide sequences encoding the same amino acid sequence as that referenced.

"Operably linked" refers to a juxtaposition wherein the components are configured so as to perform a desired function such as their natural biochemical function. Thus, control sequences or promoters operably linked to a coding sequence are capable of effecting the expression of the coding sequence.

"Heparin", "heparan sulfate" and "heparin-like compounds" are terms which are used synonymously herein. Each of the terms singly or in combination with the others is intended to encompass a large group of compounds which are generally described as sulfated polysaccharides, which includes proteoglycans and glycosaminoglycans (GAG) which are alternating copolymers of a hexosamine and an aldouronic acid. These copolymers are found in sulfated forms and are synthesized as proteoglycans and are collectively referred to as mucopolysaccharides. Other compounds such as dextran sulfate are considered "heparin-like" for purposes of the invention. Similar alternating copolymers, especially those which are highly sulfated and thus very negatively charged, are useful "heparin-like" compounds in this invention. Extensive information with respect to "heparin", "heparin-like compounds" such as glycosaminoglycans are described in detail by Benito Casu, "Structure and Biological Activity of Heparin", published in Advances in Carbohydrate Chemistry and Biochemistry, Vol. 43, pp. 51–134, which is incorporated herein by reference to disclose such compounds which might be useful in combination with certain PN-1 variants disclosed herein.

By "therapeutically effective amino acid sequence" is meant an amino acid sequence having a biological activity effective in the treatment of a disease condition. The amino acid sequence having biological activity may be an amino acid sequence of a naturally occurring protein or a portion thereof which retains the biological activity of the naturally occurring protein. Alternatively, the amino acid sequence having biological activity may be a protein, or fragment thereof retaining biological activity, which has an amino acid sequence different from the sequence of the naturally occurring protein from which if was derived.

A description of the invention is facilitated by listing the relationship between the one-letter symbols and the three-letter abbreviations for amino acids as follows:

| One-Letter Symbols Abbreviations | | Three-Letter |
|---|---|---|
| A | alanine | ala |
| C | cysteine | cys |
| D | aspartic acid | asp |
| E | glutamic acid | gln |
| F | phenylalanine | phe |
| G | glycine | gly |
| H | histidine | his |
| I | isoleucine | ile |
| K | lysine | lys |
| L | leucine | leu |
| M | methionine | met |
| N | asparagine | asn |
| P | proline | pro |
| Q | glutamine | gln |
| R | arginine | arg |
| S | serine | ser |
| T | threonine | thr |
| V | valine | val |
| W | tryptophan | trp |
| Y | tyrosine | tyr |

Amino acids have the following general structural formula

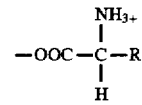

and are classified based on the chemical composition of the "R" group as follows:
1. Aliphatic
2. Hydroxyl
3. Sulfur
4. Aromatic
5. Acidic (and amides)
6. Basic
7. Imino Naturally occurring amino acids can be generally classified as being polar or non-polar as follows:
Polar S, T, C, Y, D, N, E, Q, R, H, K
Non-polar G, A, V, L, I, M, F, W, P
It is the "R" group which determines whether the amino acid will be polar or non-polar.

Amino acid residues can be generally subclassified into four major subclasses as follows:
Acidic: The residue has a negative charge due to loss of H ion at physiological pH and the residue is attracted by aqueous solution so as to seek the surface positions in the conformation of a peptide in which it is contained when the peptide is in aqueous medium at physiological pH.
Basic: The residue has a positive charge due to association with H ion at physiological pH and the residue is attracted by aqueous solution so as to seek the surface positions in the conformation of a peptide in which it is contained when the peptide is in aqueous medium at physiological pH.
Neutral/non-polar: The residues are not charged at physiological pH and the residue is repelled by aqueous solution so as to seek the inner positions in the conformation of a peptide in which it is contained when the peptide is in aqueous medium. These residues are also designated "hydrophobic" herein.

Neutral/polar: The residues are not charged at physiological pH, but the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not, and there will be an attraction for or repulsion from an aqueous medium to a greater or lesser extent. To fit the definition of "charged", a significant percentage (at least approximately 25%) of the individual molecules are charged at physiological pH. The degree of attraction or repulsion required for classification as polar or non-polar is arbitrary, and, therefore, amino acids specifically contemplated by the invention have been specifically classified as one or the other. Most amino acids not specifically named can be classified on the basis of known behavior.

Amino acid residues can be further subclassified as cyclic or noncyclic, and aromatic or nonaromatic, self-explanatory classifications with respect to the side chain substituent groups of the residues, and as small or large. The residue is considered small if it contains a total of 4 carbon atoms or less, inclusive of the carboxyl carbon. Small residues are, of course, always nonaromatic.

For the naturally occurring protein amino acids, subclassification according to the foregoing scheme is as follows:
Acidic: Aspartic acid and Glutamic acid;
Basic/noncyclic: Arginine, Lysine;
Basic/cyclic: Histidine;
Neutral/polar/small: Threonine, Serine and Cysteine;
Neutral/polar/large/nonaromatic: Threonine, Asparagine, Glutamine;
Neutral/polar/large/aromatic: Tyrosine;
Neutral/non-polar/small: Alanine;
Neutral/non-polar/large/nonaromatic: Valine, Isoleucine, Leucine, Methionine;
Neutral/non-polar/large/aromatic: Phenylalanine and Tryptophan.
Proline The gene-encoded amino acid proline, although technically within the group neutral/non-polar/large/cyclic and nonaromatic, is a special case due to its known effects on the secondary conformation of peptide chains, and is not, therefore, included in this defined group, but is included as a group of its own.

Other amino acid substitutions for those encoded in the gene can also be included in peptide compounds within the scope of the invention and can be classified within this general scheme.

Variants of the invention may include commonly encountered amino acids, which are not encoded by the genetic code, for example, β-alanine (β-ala), or other omega-amino acids, such as 3-amino propionic, 4-amino butyric and so forth, α-aminoisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), cysteic acid (Cya) and methionine sulfoxide (MSO). These also fall conveniently into particular categories.

Based on the above definition,
Sar and β-ala are neutral/non-polar/small;
t-BuA, t-BuG, N-MeIle, Nle and Cha are neutral/non-polar/large/nonaromatic;
Orn is basic/noncyclic;
Cya is acidic;
Cit, Acetyl Lys, and MSO are neutral/polar/large/nonaromatic; and
Phg is neutral/non-polar/large/aromatic.

Both L and D isomers of amino acids encoded by the genetic code or otherwise are included as amino acids useful in this invention provided the resulting protein processes the required activity.

The various omega-amino acids are classified according to size as neutral/non-polar/small (β-ala, i.e., 3-aminopropionic, 4-aminobutyric) or large (all others).

The nomenclature used to describe compounds of the present invention follows the conventional practice wherein the amino group is assumed to be to the left and the carboxyl group to the right of each amino acid in the peptide. In the formulas representing selected specific embodiments of the present invention, the amino- and carboxyl-terminal groups, although often not specifically shown, will be understood to be in the form they would assume at physiological pH values, unless otherwise specified. Thus, the N-terminal $NH^+_3$ and C-terminal $OH^-$ at physiological pH are understood to be present though not necessarily specified and shown, either in specific examples or in generic formulas.

Cysteine-PEGylated Proteins

Chemically modified proteins, and more specifically cysteine-PEGylated proteins, suitable for therapeutic applications are produced by attaching polyethylene glycol to a cysteine residue within the protein. To obtain the desired result of a stable, biologically active compound the PEG must be attached in a specific manner. First, one may attach the polyethylene glycol to a cysteine residue present at or near a site which is normally glycosylated. Preferably, the specific amino acid modified by glycosylation (e.g., asparagine in N-linked glycosylation or serine or threonine in O-linked glycosylation) is replaced by a cysteine residue, which is subsequently chemically modified by attachment of PEG. Generation of cysteine-containing mutants can be accomplished by, for example, site-directed mutagenesis using methods well known in the art (Kunkel, T. A. (1988) in *Nucleic Acids and Molecular Biology*, Eckstein, F. Lilley, D. M. J., eds., Springer-Verlag, Berling and Heidelberg, vol. 2, p. 124). In addition, if the protein of interest is one member of a family of structurally related proteins, glycosylation sites for any other member can be matched to an amino acid on the protein of interest, and that amino acid changed to cysteine for attachment of the polyethylene glycol. Alternatively, if a crystal structure has been determined for the protein of interest or a related protein, surface residues away from the active site or binding site can be changed to cysteine for the attachment of polyethylene glycol.

The strategy of the invention for identification of good PEG attachment sites has the advantage that one does not require knowledge of the proteins three dimensional structure. Moreover, the strategy also takes advantage of the selective power of evolution, which has served to select against inappropriate sites for modification. Nature has chosen to add glycosylation residues to the surface of secreted proteins to aid stability and increase serum half-life. For example, asparagine residues are glycosylated when part of a well known N-glycosylation signal: N[!P]S/T[!P], where N is asparagine, !P is any amino acid except proline, T is threonine, and S is serine. Replacement of these Asn residues by cysteine, followed by cysteine-specific PEGylation, produces proteins with significantly increased serum half-life with a minimum loss in activity.

Alternatively, an amino acid residue normally modified by O-linked glycosylation can be replaced by a cysteine residue to which PEG is then attached. To date, this is the closest thing to in vitro glycosylation, and in some respects may be better since glycosylation with inappropriate sugar residues may lead to increased clearance from the serum by the liver, whereas PEG residues are substantially inert.

If a higher degree of PEG modification is desired and the protein to be modified is one member of a family of structurally related proteins, other members of the same family will often have one or more sites of glycosylation not found in the protein of interest. If these "new" potential sites are in a region which is reasonably conserved (i.e., not part of an insertion or with a sequence which is so different that it is likely to have a different structure) it is expected that replacement of the residue equivalent to the Asn with cysteine followed by PEGylation will result in a more highly PEG modified protein without significant loss in activity. Portions of mutant proteins which retain sufficient activity can be combined to generate a single fusion protein with multiple PEG attachment sites.

If a further higher degree of PEG modification is required, and/or if the protein to be chemically modified is not normally glycosylated, other solvent accessible residues can be changed to cysteine, and the resultant protein subjected to PEGylation. Appropriate residues can easily be determined by those skilled in the art. For instance, if a three-dimensional structure is available for the protein of interest, or a related protein, solvent accessible amino acids are easily identified. Also, charged amino acids such as Lys, Arg, Asp and Glu are almost exclusively found on the surface of proteins. Substitution of one, two or many of these residues with cysteine will provide additional sites for PEG attachment. In addition, amino acid sequences in the native protein which are recognized by antibodies are usually on the surface of the protein. These and other methods for determining solvent accessible amino acids are well known to those skilled in the art.

Proteins modified by the cysteine-PEGylation methods of the invention will preferably retain at least 25%, more preferably at least 50%, even more preferably between about 50% to 75%, most preferably 100% of the biological activity associated with the unmodified protein. Where the modified protein contains cysteine residues which are not present in the naturally-occurring protein, the modified cysteine-PEGylated protein will exhibit at least 25%, more preferably at least 50%, even more preferably between about 50% to 75%, most preferably about 100% of the biological activity associated with the unmodified, naturally-occurring protein. Preferably, the cysteine-PEGylated proteins have a half-life ($t_{1/2}$) which is enhanced relative to the half-life of the unmodified protein from which it was derived. Preferably, the half-life of the cysteine-PEGylated protein is enhanced by at least 1.5-fold to 2-fold, more preferably by about 2-fold to 3-fold, even more preferably by about 5-fold to 10-fold, optimally about 100-fold, usually about 6-fold relative to the half-life of the unmodified parent protein.

Thus, cysteine-PEGylated proteins of the invention may have an amino acid sequence which is the same as the amino acid sequence of the naturally-occurring protein or different therefrom. In general, cysteine-PEGylated proteins may be generated by covalently binding (i.e., coupling) PEG to any protein, protein fragment, or peptide having biological activity and for which increased biological stability is desired. Of particular interest are those proteins, protein fragments, and peptides which are useful in therapeutic applications, such as serine protease inhibitor proteins, growth factors, and cytokines. The proteins PN-1, human growth hormone (hGH), erythropoietin (EPO), and antithrombin-III (ATIII) are of particular interest. Specific, exemplary proteins of interest, as well as exemplary classes of proteins, which can be modified using the methods of the invention are provided in Table 1A.

TABLE 1A

Exemplary Proteins and Protein Classes for Generation of Cysteine-PEGylated Proteins

SPECIFIC EXEMPLARY PROTEINS

| | |
|---|---|
| interferon-α2A | insulin-like growth factor-1 (IGF-1) |
| interferon-α2B | insulin |
| human growth hormone (hGH) | transforming growth factor (TGF) |
| erythropoietin (EPO) | ciliary neurite transforming factor (CNTF) |
| thrombopoietin (TPO) | brain-derived neurite factor (BDNF) |
| IL-1 | insulintropin |
| IL-2 | glial-derived neurite factor (GDNF)* |
| IL-1 RA | tissue plasminogen activator (tPA) |
| superoxide dismutase (SOD) | urokinase |
| catalase | streptokinase |
| fibroblast growth factor (FGF) (acidic or basic) | hemoglobin |
| neurite growth factor (NGF) | adenosine deamidase |
| granulocyte macrophage colony stimulating factor (GM-CSF) | bovine growth hormone (BGH) |
| granulocyte colony stimulating factor (G-CSF) | calcitonin |
| platelet derived growth factor (PDGF) | bactericidal/permeability increasing protein (BPI) |
| L-asparaginase | arginase |
| uricase | phenylalanine |
| γ-interferon | ammonia lyase |

EXEMPLARY CLASSES OF PROTEINS

| | |
|---|---|
| proteases | pituitary hormones |
| protease inhibitors | growth factors |
| cytokines | somatomedians |
| chemokines | immunoglobulins |
| gonadotrophins | interleukins |
| chemotactins | interferons |
| lipid-binding proteins | allergens |

*GDNF is the same protein as protease nexin-1 (PN-1).

Cysteine-PEGylated proteins are created by attaching polyethylene glycol to a thio group on a cysteine residue of the protein. The PEG moiety attached to the protein may range in molecular weight from about 200 to 20,000 MW. Preferably the PEG moiety will be from about 1,000 to 8,000 MW, more preferably from about 3,250 to 5,000 MW, most preferably about 5,000 MW.

The actual number of PEG molecules covalently bound per chemically modified protein of the invention may vary widely depending upon the desired protein stability (e.g. serum half-life) and the protein used for chemical modification. For relatively small proteins, which generally have short half-lives, it may be desirable to PEGylate the protein so as to increase the protein's total molecular weight to 30,000–40,000 MW or more. Because smaller proteins may have fewer available PEGylation sites, the PEG moiety used in PEGylation will preferably be of a higher molecular weight.

The chemically modified proteins contain at least one PEG moiety, preferably at least two PEG moieties, up to a maximum number of PEG moieties bound to the protein without abolishing activity, e.g., the PEG moiety(ies) are bound to an amino acid residue which is on the sruface of the protein and/or away from the active site. The ratio of PEG to protein is preferably 1:1, more preferably 2:1, even more preferably 5:1, up to a 10:1 or 40:1 ratio of PEG molecules to protein. Preferably the chemically modified protein composition produced by the subject invention will be homogeneous with respect to the position of the cysteine residue (s) modified and the number of cysteine residue(s) modified.

General methods of attaching polyethylene glycol to proteins are disclosed within U.S. Pat. No. 4,179,337 issued Dec. 18, 1979 (incorporated herein by reference to disclose methods of attaching polyethylene glycol to proteins). Further, other methods of attaching polyethylene glycol are disclosed within U.S. Pat. No. 5,122,614 issued Jun. 16, 1992, also incorporated herein by reference to disclose methods of attaching polyethylene glycol to proteins. Maleimido-PEG is perhaps the most useful reagent for cysteine-PEGylation, but other chemistries are available for specific cysteine modification.

It has also been found that it is possible to attach other groups to the thio group of the cysteine residue. For example, the protein may be biotinylated by attaching biotin to a thio group of a cysteine residue. Examples of cysteine-PEGylated proteins of the invention, as well as proteins having a group other than PEG covalently attached via a cysteine residue according to the invention, are as follows:

TABLE 2

| Record # | NCY | mutation | sequence | indication |
| --- | --- | --- | --- | --- |
| 1 | NCY2601 | PEG-PN1 | lys-modified | long half-life |
| 2 | NCY2611 | Biotin-PN1 | lys-modified | detection/coupling |
| 3 | NCY2621 | PEG-PN1 | cys-modified | long half-life |
| 4 | NCY2631 | Biotin-PN1 | cys-modified | detection/coupling |

Of the above examples, records numbers 1 and 2 are of a general type known in the art in that the polyethylene glycol or biotin is attached to lysine position of the peptide. However, record numbers 3 and 4 are, respectively, examples wherein the polyethylene glycol or biotin are connected at a cysteine group. The importance of such is described further below.

Modification of proteins with PEG can also be used to generate dimers and multimeric complexes of proteins, fragments, and/or peptides which have increased biological stability and/or potency. These dimeric and multimeric proteins of the invention may be naturally occurring dimeric or multimeric proteins. For example, the dimer or multimer may be composed of cross-linked subunits of a protein (e.g., hemoglobin). Alternatively, the dimeric and multimeric proteins may be composed of two proteins which are not normally cross-linked (e.g., a dimer of cross-linked EPO protein).

Dimeric proteins of the invention may be produced by reacting the protein with (Maleimido)$_2$-PEG, a reagent composed of PEG having two protein-reactive moieties. This PEGylation reaction with the bi-functional PEG moiety generates dimers of the general formula:

where $R_1$ and $R_2$ may represent the same or different proteins and S represents the thio group of a cysteine either present in the native $R_1$ or $R_2$ protein, or introduced by site-directed mutagenesis. The proteins $R_1$ and $R_2$ may each vary in size from about 6 to 1,000 amino acids, preferably about 20 to 400 amino acids, more preferably 40 to 200 amino acids. In dimeric molecules, $R_1$ and $R_2$ are preferably from about 100 to 200 amino acids. Dimers and multimers of particular interest include those composed of proteins, protein fragments and/or peptides which are less than about 40,000 molecular weight.

Where the protein contains (or is engineered to contain) more than one free cysteine, multimeric proteins where the proteins (represented by $R_1$, $R_2$, ... $R_n$) may be the same or different can be generated. The proteins represented by $R_1$, $R_2$, ... $R_n$ may vary in size from about 6 to 1,000 amino acids, preferably 20 to 400 amino acids, more preferably 40 to 200 amino acids. Such multimeric proteins may be of the following general formula:

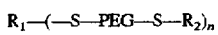

where $R_1$ represents the protein having multiple free cysteines, for example from 2 to 20 free cysteines, usually from 5 to 7 free cysteines. $R_2$ may represent a protein the same as or different from $R_1$. Furthermore, each of the $R_2$ proteins attached to $R_1$ may be the same proteins, or represent several different proteins.

The degree of multimeric cross-linking can be controlled by the number of cysteines either present and/or engineered into the protein, and by the concentration of (Maleimido)$_2$PEG used in the reaction mixture. In addition, the Maleimido-PEG and (Maleimido)$_2$-PEG reagents may be used in the same reaction with proteins for formation of couplings of proteins having single PEG moieties as well as PEG cross-links between proteins within the complex. The dimeric or multimeric protein generated will have an increased half-life relative to the native protein, due at least in part to its increased size relative to the native protein. Such larger proteins are not degraded or cleared from the circulation by the kidneys as quickly as are smaller proteins. In addition, activity or potency of the dimeric or multimeric protein may be increased.

Dimeric and multimeric proteins may be generated by reaction with Maleimido-PEG or (Maleimido)$_2$-PEG. Exemplary proteins for dimeric and/or multimeric complex formation using the method of the invention include PN-1, PN-1 variants, hemoglobin, and erythropoietin (EPO), as well as any of the proteins or members of the protein classes exemplified in Table 4A. Preferably, the protein generated by the method of the invention is a PEGylated cross-linked complex of the "a" and "b" chains of hemoglobin. Multimeric complexes of hemoglobin having intermolecular and/or intramolecular cross-links may also be generated by the subject method.

In general, the method of identifying cysteine residues for PEG modification, and/or identifying amino acid residues to be replaced with cysteine which are subsequently modified by attachment of PEG, provides for generation of a PEGylated protein which can be reasonably expected to retain most or all of the activity of the native protein. The sites selected for modification and/or substitution with cysteine are selected on the basis of the structure of the protein, i.e. the selected sites are solvent accessible residues which are not involved in the active site.

The effect of mutations located outside of the active site are generally predictable in that they generally do not change the primary activity of the protein. In addition, the structural mutations described herein are within solvent-accessible regions of the protein (i.e. on the protein "surface") which have limited or no interaction with other residues in the protein molecule. Thus, mutations at these positions are unlikely to affect the conformation of any other amino acid in a protein.

The method of PEGylation of the invention described herein is intended to be a general procedure and as such is applicable to any protein to increase solubility, circulating half life and/or to decrease immunogenicity.

Exemplary Proteins for PEGylation: Serine Proteases and their Inhibitors (Serpins)

Although originally named for their mechanism of action, members of the serine protease family also show significant sequence and structural homology. Some serine proteases are very specific, cleaving only certain peptide bonds of a specific target protein while others are very nonspecific, degrading multiple target proteins into small peptides.

Serine proteases are regulated at many levels. Some are synthesized as inactive proenzymes and are activated only during specific events and at specific locations. This allows the body to respond rapidly to a physiological perturbation by activating an already present reservoir of proteolytic activity. Coagulation, for example, is carried out when circulating proenzymes such as Factor X and prothrombin are sequentially activated in response to injury resulting in a cascade of clotting activity. In addition, proteolytic activity is often localized to specific sites, such as receptor binding sites which can cause high local concentrations of protease or proenzyme ready for activation.

Once activated, it is extremely important that proteolytic activity be confined both spatially and temporally. This control is often achieved by the presence of specific inhibitors which block proteolytic activity. An important family of related proteins, the serine protease inhibitors, or "serpins", are key in the regulation of serine proteases. Like the serine proteases, serpins were first defined by their common mechanism of action but later turned out to be highly homologous both in terms of sequence and structure.

Serpins all contain an inhibitor domain with a reactive peptide bond defined on either side by the variables $P_1$ and $P_1'$. In a direction to the left away from the reactive site, the amino acids are referred to as $P_1$, $P_2$, $P_3$, etc., and in a direction to the right away from the reactive site they are referred to as $P_1'$, $P_2'$, $P_3'$, etc. The $P_1$ residue is recognized by the substrate binding pocket of the target protease which attacks the reactive peptide bond as though a normal substrate. However, hydrolysis of the peptide bond and release of the protease does not proceed to completion. The normal deacylation step is so slow that the reaction becomes essentially irreversible and the protease becomes trapped in a stable, equimolar complex.

In order to provide examples of the present invention, the inventors have focused on the serine protease Protease Nexin-1 (PN-1) purified from serum-free medium conditioned by human foreskin cells (Scott, R. W. et al., *J. Biol. Chem.* (1983) 58:10439–10444). PN-1 is a 42 kDa glycoprotein which is produced by fibroblasts, myotubes, heart muscle cells, vascular smooth muscle cells, glial cells, platelets, and macrophages. Its release, along with that of plasminogen activator, is stimulated by phorbol esters and by mitogens (Eaton, D. L. et al., *J. Cell. Biol.* (1983) 123:128). Native PN-1 is an approximately 400 amino acid protein containing about 10% carbohydrate. Since it is present only in trace levels in serum, it apparently functions at or near the surfaces of interstitial cells. PN-1 inhibits all the known activators of urokinase proenzyme, plasmin, trypsin, thrombin, and Factor Xa (Eaton, D. L. et al., *J. Biol. Chem.* (1984) 259:6241). It also inhibits tissue plasminogen activator and urokinase. However, PN-1 does not inhibit elastase or cathepsin G.

PN-1 is different from most serpins in that it is found in tissues, contains a high affinity heparin binding site which localizes it to tissues, and has a tissue clearance receptor that is responsible for endocytosis of protease-PN-1 complexes. We provide variants and methods of producing such variants which have polyethylene glycol specifically attached to one or more cysteine residues, such cysteine residues being either present in the parent molecule or introduced on the surface of the protein by site-directed mutagenesis, and methods for determining appropriate sites for the introduction of cysteine residues.

PN-1 is very similar, both structurally and functionally to antithrombin (AT-III). AT-III is the primary plasma inhibitor of blood coagulation. The inhibition of thrombin by AT-III in plasma is normally very weak but is accelerated significantly by the presence of heparin or by other mucopolysaccharides on the endothelial lining of blood vessels. The therapeutic value of heparin as a blood "thinning" agent is due to its enhancement of AT-III activity. Like AT-III, PN-1 has a high affinity heparin binding site and inhibits thrombin much more rapidly (50–100 fold) in the presence of heparin. Thus PN-1 has therapeutic potential as an anticoagulant.

On the other hand, PN-1 differs from AT-III in a number of ways. Unlike AT-III, PN-1 is also a good inhibitor of the fibrinolytic enzymes urokinase and plasmin, as well as trypsin. Furthermore, PN-1 is not found in significant quantities in plasma and may function primarily in the tissues. The high affinity heparin binding site of PN-1 serves to localize it to connective tissues and cells which contain sulfated proteoglycans on their surface and surrounding extracellular matrix. Thus PN-1's primary role seems to be in regulating proteolytic activity in tissues as opposed to blood. Further evidence for the role of PN-1 is found by the fact that it is present in brain tissue and may be involved in peripheral nerve regeneration and neurite extension.

The relative efficiency with which PN-1 inhibits serine proteases can be measured by the second order association rate constant ($k_{ass}$) as previously described in Bieth, J. G. (*Bull. Euro. Physiopath. Resp.* (1980) 16:183–195), and reported by Scott et al. (*J. Biol. Chem.* (1985) 260:7029–7034), both of which are incorporated herein by reference to disclose and explain the meaning of the rate association constant. In general, a value for $k_{ass}$ equal to or greater than $1 \times 10^5$ $M^{-1}S^{-1}$ for a particular protease-inhibitor reaction is considered to be physiologically significant (*Travis and Salveson Ann. Rev. Biochem.* (1983) 52:655–709). The $k_{ass}$ or rate association constant has inverse-mole-seconds as its units, and the larger the $k_{ass}$, the more rapid the inhibition. Accordingly, a $k_{ass}$ value is always given as a value with respect to a particular enzyme and is zero if there is no inhibition of the enzyme.

Many physiologically important protease-inhibitor reactions such as elastase-α-1 antitrypsin and plasmin-α-2-antiplasmin occur with rate constants as high as $1 \times 10^7$ $M^{-1}S^{-1}$ or greater. The thrombin-PN-1 reaction occurs at a similar high rate in the presence of heparin.

Description of PN-1 (α and β)

FIGS. 1A to 1B and FIGS. 2A to 2B, respectively, show the amino acid sequence of PN-1α and PN-1β. The α and β forms differ by the substitution of thr$_{310}$-gly$_{311}$ in PN-1β for arg$_{310}$ in PN-1α. Alignment of the reactive site center of PN-1 with other serpins, such as antithrombin III, predicts that arginine 345 (346 for PN-1β) is the reactive site center or "$P_1$" site. The "$P_1$" site (arginine at position 345 for PN-1α and 346 for PN-1β) has been confirmed by sequencing of the peptide fragment released from PN-1 upon dissociation of complexes with thrombin. Furthermore, PN-1 normally inhibits only enzymes which cleave at arginine (the $P_1$ residue), such as thrombin, plasmin, trypsin, plasminogen activators, and plasma kallikrein.

Based on the above and by referring to the sequences of PN-1α and PN-1β shown in FIGS. 1A to 1B and FIGS. 2A to 2B respectively, it can be seen that the "$P_1$'" site is serine at position 346 for PN-1α and serine at position 347 for PN-1β.

Description of Protease Inhibitor Action

In order to allow the body to respond rapidly, several serine proteases are synthesized at relatively high levels in their inactive proenzyme forms and are only activated during specific events. For example, coagulation is carried out when circulating proenzymes such as Factor X and prothrombin are sequentially activated in response to an injury. This activation results in a cascade of clotting activity. Proteolytic activity is often localized to specific sites such as receptor binding sites. Once a proteolytic enzyme is activated, it is extremely important that the enzyme activity be confined both spatially and temporally. Such confinement is in part brought about by the inhibitory effect of serpins.

All serpins contain an inhibitor domain with a reactive peptide bond defined on either side by $P_1$ and $P_1'$ residues. The $P_1$ residue (such as arginine at position 345 for PN-1α and 346 for PN-1β) is recognized by the substrate binding pocket of the target protease. Upon recognition of the "reactive" site (of the inhibitor by the protease) the protease attacks the reactive peptide bond of the inhibitor as if it were a normal substrate. However, in the case of serpin hydrolysis of the peptide bond and release of the protease does not proceed to completion. The normal deacylation step is so slow that the reaction becomes essentially irreversible and the protease becomes trapped with the inhibitors in a stable, covalent, equal molar complex. Since the $P_1$ residue is the predominant determinant residue recognized by the substrate binding pocket of the target protease, alteration of this residue can alter the protease specificity of the inhibitor entirely or substantially change the degree of the inhibitory effect obtainable. Residues near the $P_1$ residue (i.e., $P_4$–$P_4'$) also contribute to protease specificity. Accordingly, alteration of these residues can also lead to modified inhibitory effects.

In order to provide specific examples of proteins which may be modified by cysteine-PEGylation according to the invention, PN-1, PN-1 variants containing single-site mutations in the active site, PN-1 variants having multiple site mutations within the active site, PN-1 variants having the active site of a different serine protease, PN-1 variants containing a sequence for binding the substrate normally bound by the target protease, and PN-1 chimeric proteins for cysteine-PEGylation are described herein.

PN-1 Variants—Active Site Manipulation

PN-1 variants exemplified herein may have single site mutations within the active site described above, multiple mutations within the active site, have the active site replaced with the active site of another serpin, or a chimeric protein composed of PN-1 (or a portion thereof) fused to a second protein. Methods for producing such variants and the activity of exemplary variants so produced are described in co-pending application PCT/US94/11624, filed Oct. 18, 1994, and in U.S. Pat. No. 5,187,089, issued Feb. 16, 1993, both of which are incorporated herein by reference as to the production and description of various PN-1 variants.

PN-1 Having Single-Site or Multiple-Site Mutations Within the Active Site

One approach to producing PN-1 variants is to substitute one of the sites with a residue which is substantially different from the residue present, such as including a non-polar residue in place of a polar residue while substituting the other site with a residue which is substantially similar to the residue present there both in terms of being polar or non-polar and in terms of having a similar "R" group. Another approach is to substitute both sites with residues which are substantially different from the original residues. Yet another possible means for producing variants would be to use either of the above-suggested strategies in combination with substituting other sites. A variety of such substitutions will occur to those skilled in the art upon reading this disclosure. What is important is that the resulting variant continued to provide activity. The ability of the variant to provide activity will depend on the substrate specificity. Accordingly, the present invention is intended to encompass single, double and multiple substitutions of the residues to provide variants which continue to have activity with respect to a given protease or gain substantial activity with respect to another protease.

In connection with the present invention, the PN-1 variants which have activity are variants which have (1) substantially increased potency with respect to inhibiting tPA, urokinase, and/or other related enzymes; (2) substantially increased potency with respect to inhibiting elastase; or most preferably (3) substantially increased potency with respect to inhibiting elastase and which potency is still further increased dramatically in the presence of heparin. In that the present invention has demonstrated that it is possible to produce PN-1 variants which inhibit elastase and has further demonstrated that it is possible to produce such variants which not only inhibit elastase, but have substantially increased potency to inhibit elastase in the presence of heparin others skilled in the art of such inhibitors will be able to deduce other variants which are intended to be within the scope of the present invention.

Specific PN-1 Variants

Examples of protease nexin-1 variants of the invention are listed in Table 3 along with "indication" of the variant.

TABLE 3

| Record # | NCY | mutation | sequence | indication |
|---|---|---|---|---|
| 1 | NCY2000 | CHO PN-1 | TTAILIAR–SSPP | |
| 2 | NCY2001 | P1Ala | | |
| 3 | NCY2002 | P1Arg (WT) | | |
| 4 | NCY2003 | P1Asn | | |
| 5 | NCY2004 | P1Asp | | |
| 6 | NCY2005 | P1Cys | | |
| 7 | NCY2006 | P1Gln | | |
| 8 | NCY2007 | P1Glu | | |
| 9 | NCY2008 | P1Gly | | |
| 10 | NCY2009 | P1His | | |
| 11 | NCY2010 | P1Ile | | antielastase |
| 12 | NCY2011 | P1Leu | | antielastase |
| 13 | NCY2012 | P1Lys | | antiplasmin |
| 14 | NCY2013 | P1Met | | |
| 15 | NCY2014 | P1Phe | | |
| 16 | NCY2015 | P1Pro | | |
| 17 | NCY2016 | P1Ser | | |
| 18 | NCY2017 | P1Thr | | |
| 19 | NCY2018 | P1Trp | | |
| 20 | NCY2019 | P1Tyr | | |
| 21 | NCY2020 | P1Val | | antielastase |
| 22 | NCY2021 | P2Ala (WT) | | |
| 23 | NCY2022 | P2Arg | | |
| 24 | NCY2023 | P2Asn | | |
| 25 | NCY2024 | P2Asp | | |
| 26 | NCY2025 | P2Cys | | |
| 27 | NCY2026 | P2Gln | | |
| 28 | NCY2027 | P2Glu | | |

TABLE 3-continued

| Record # | NCY | mutation | sequence | indication |
|---|---|---|---|---|
| 29 | NCY2028 | P2Gly | | faster kinetics |
| 30 | NCY2029 | P2His | | |
| 31 | NCY2030 | P2Ile | | |
| 32 | NCY2031 | P2Leu | | |
| 33 | NCY2032 | P2Lys | | |
| 34 | NCY2033 | P2Met | | |
| 35 | NCY2034 | P2Phe | | |
| 36 | NCY2035 | P2Pro | | faster kinetics |
| 37 | NCY2036 | P2Ser | | |
| 38 | NCY2037 | P2Thr | | |
| 39 | NCY2038 | P2Trp | | |
| 40 | NCY2039 | P2Tyr | | |
| 41 | NCY2040 | P2Val | | |
| 42 | NCY2041 | P3Ala | | |
| 43 | NCY2042 | P3Arg | | |
| 44 | NCY2043 | P3Asn | | |
| 45 | NCY2044 | P3Asp | | |
| 46 | NCY2045 | P3Cys | | |
| 47 | NCY2046 | P3Gln | | |
| 48 | NCY2047 | P3Glu | | |
| 49 | NCY2048 | P3Gly | | |
| 50 | NCY2049 | P3His | | |
| 51 | NCY2050 | P3Ile (WT) | | |
| 52 | NCY2051 | P3Leu | | |
| 53 | NCY2052 | P3Lys | | |
| 54 | NCY2053 | P3Met | | |
| 55 | NCY2054 | P3Phe | | |
| 56 | NCY2055 | P3Pro | | |
| 57 | NCY2056 | P3Ser | | |
| 58 | NCY2057 | P3Thr | | |
| 59 | NCY2058 | P3Trp | | |
| 60 | NCY2059 | P3Tyr | | |
| 61 | NCY2060 | P3Val | | |
| 62 | NCY2101 | P1'Ala | | |
| 63 | NCY2102 | P1'Arg | | |
| 64 | NCY2103 | P1'Asn | | |
| 65 | NCY2104 | P1'Asp | | |
| 66 | NCY2105 | P1'Cys | | |
| 67 | NCY2106 | P1'Gln | | |
| 68 | NCY2107 | P1'Glu | | |
| 69 | NCY2108 | P1'Gly | | |
| 70 | NCY2109 | P1'His | | |
| 71 | NCY2110 | P1'Ile | | anti-Factor Xa |
| 72 | NCY2111 | P1'Leu | | |
| 73 | NCY2112 | P1'Lys | | |
| 74 | NCY2113 | P1'Met | | |
| 75 | NCY2114 | P1'Phe | | |
| 76 | NCY2115 | P1'Pro | | |
| 77 | NCY2116 | P1'Ser (WT) | | |
| 78 | NCY2117 | P1'Thr | | anti-Factor Xa |
| 79 | NCY2118 | P1'Trp | | |
| 80 | NCY2119 | P1'Tyr | | |
| 81 | NCY2120 | P1'Val | | |

The above examples 1–81 represent the substitution at different sites within the active site of PN-1. For example, record nos. 2–21 represent a substitution at the $P_1$ position of PN-1. The indication "WT" is provided to indicate the naturally-occurring or wild-type sequence produce via CHO cells. As is evident from this disclosure, the examples could be continued to include all 20 amino acid substitutions at each position within the active site, that is, all 20 naturally-occurring amino acids could be substituted, using site-directed mutagenesis, at positions $P_1$, $P_2$, $P_3$, $P_4$, $P_1'$, $P_2'$, $P_3'$, and $P_4'$.

It is possible to produce individual, single-site variants using site-directed mutagenesis. However, it is also possible to produce large numbers of Type I variants at the same time. For example, it is possible to produce the 64 million different variants simultaneously wherein all of the 20 naturally occurring amino acids are substituted at all 8 positions. Such can be carried out using a phage display synthesis methodology as disclosed within U.S. Pat. No. 5,223,409 issued Jun. 29, 1993. Further, the chemical synthesis methodology disclosed within U.S. Pat. No. 5,010,175 issued Apr. 23, 1991 can be used to produce such large mixtures of variants. Different types of screening methodology such as that disclosed within U.S. Pat. No. 5,223,409 can then be used to screen the variants to determine particular activities.

As an example of the activity of a PN-1 variant having a mutation within the active site, the R345I variant is described below. The R345I variant (which has isoleucine substituted for arginine at position 345 of PN-1α, and at the equivalent position 346 in PN-1β) has an inhibitory effect against elastase. Naturally-occurring PN-1 has no inhibitory activity against elastase. Furthermore, this activity by the R345I variant is increased approximately two orders of magnitude in the presence of heparin. The activity of the R345I variant (also termed NCY2010) against a panel of proteases, ad the second-order rate constants with respect to each protease, is provided below.

TABLE 4

PN-1 ($P_1$Ile)
NCY 2010

| Protease | Second Order Rate Constant ($M^{-1}S^{-1}$) |
|---|---|
| 1) Thrombin | <100 |
| 2) Plasmin | — |
| 3) Plasmin (hp) | — |
| 4) Xa | — |
| 5) Xa (hp) | — |
| 6) Urokinase | — |
| 7) Urokinase (hp) | — |
| 8) Kallikrein | <100 |
| 9) Cathepsin G | <100 |
| 10) Activated protein C | — |
| 11) Activated protein C (hp) | — |
| 12) Elastase | $4.15 \times 10^6$ |

(hp) indicates in the presence of 10 μg/ml of heparin.

Serpin Active Site "Swap" Variants

PN-1 variants having an active site of another serpin are produced in a manner similar to the singe and multiple site PN-1 variants described above. However, the active site of PN-1 is modified in a manner so that it matches the sequence of the active site of another protease, and preferably another serpin. Examples of active site swap PN-1 variants include the following:

TABLE 5

| NCY# | Serpin | $P_4$ | $P_3$ | $P_2$ | $P_1$ | $P_1'$ | $P_2'$ | $P_3'$ | $P_4'$ | |
|---|---|---|---|---|---|---|---|---|---|---|
| | Protease Nexin-1 | Leu— | Ile— | Ala— | Arg | Ser— | Ser— | Pro— | Pro | |
| 2203 | PAI-1 | Val— | Ser— | Ala— | Arg | Met— | Ala— | Pro— | Glu | |
| 2204 | PAI-2 | Met— | Thr— | Gly— | Arg | Thr— | Gly— | His— | Gly | (x) |

TABLE 5-continued

| NCY# | Serpin | P4 | P3 | P2 | P1 | P1' | P2' | P3' | P4' | |
|------|--------|-----|-----|-----|-----|-----|-----|-----|-----|---|
| 2205 | PAI-3* | Phe— | Thr— | Phe— | Arg | Ser— | Ala— | Arg— | Leu | |
| 2201 | ATIII | Ile— | Ala— | Gly— | Arg | Ser— | Leu— | Asn— | Pro | |
| 2206 | α2-anti-plasmin | Ala— | Met— | Ser— | Arg | Met— | Ser— | Leu— | Ser | |
| 2207 | C1-inhibitor | Ser— | Val— | Ala— | Arg | Thr— | Leu— | Leu— | Val | |
| 2208 | Kallikrein BP | Ile— | Leu— | Ser— | Arg | Arg— | Thr— | Ser— | Leu | OR |
| 2209 | (rat) | Phe— | Arg— | Ile— | Leu | Ser— | Arg— | Arg— | Thr | |
| 2210 | α1AT | Ala— | Ile— | Pro— | Met | Ser— | Ile— | Pro— | Pro | |
| 2211 | α1AT related | Glu— | Lys— | Ala— | Trp | Ser— | Lys— | Tyr— | Gln | |
| 2212 | α1AC | Leu— | Leu— | Ser— | Ala | Leu— | Val— | Glu— | Thr | OR |
|      |        | Ile— | Thr— | Leu— | Leu | Ser— | Ala— | Leu— | Val | |
| 2202 | HCII | Phe— | Met— | Pro— | Leu | Ser— | Thr— | Glu— | Val | |
| 2213 | urokinase inh. | Met— | Thr— | Gly— | Arg | Thr— | Gly— | His— | Gly | ⓧ |

ⓧ indicates the sequence is preferably followed by —Gly—Pro
Underlining residues indicates a difference from the natural PN-1 sequence.
This table is meant as an example and should not be considered limiting of active site swap PN-1 variants.

The same methodology referred to above with respect to single and multiple site PN-1 variants can be used in the production of active site swap PN-1 variants. Further, the methodology disclosed within the above-cited patents (incorporated herein by reference) can be used to produce active site swap PN-1 variants. The methodology is modified only by first determining the active site of another serpin. After determining the amino acid sequence of the active site of a different serpin and studying the activity of that different serpin it is possible to produce an active site swap variant having a particular and desired changed activity as compared with the naturally occurring PN-1. The activity of the variants produced is tested as described above for the single and multiple site PN-1 variants. An exemplary active site swap PN-1 variants and its activity against a panel of protease is provided below:

TABLE 6

2201 (AT III)

| Protease | Second Order Rate Constant (M$^{-1}$S$^{-1}$) |
|----------|-----------------------------------------------|
| 1) Thrombin | 1.69 × 10$^4$ |
| 2) Plasmin | 2.74 × 10$^4$ |
| 3) Plasmin (hp) | 4.45 × 10$^4$ |
| 4) Xa | 4.21 × 10$^3$ |
| 5) Xa (hp) | 2.98 × 10$^4$ |
| 6) Urokinase | <100 |
| 7) Urokinase (hp) | — |
| 8) Kallikrein | 9.49 × 10$^4$ |
| 9) Cathepsin G | <100 |
| 10) Activated protein C | <100 |
| 11) Activated protein C (hp) | — |
| 12) Elastase | — |

(hp) indicates in the presence of 10 μg/ml of heparin.

Variants Having a Substrate Sequence of a Protease

PN-1 variants having a different substrate sequence are produced by first determining the substrate sequence of a protease. The substrate sequences of some proteases which are known and which would be useful in connection with the present invention are provided below in Table 3A.

TABLE 7

| PROTEASE | substrate sequence |
|----------|-------------------|
| Thrombin | D—Phe—Pip—Arg—pNA |
|          | Ts—Gly—Pro—Arg—pNA |
| Factor Xa | bz-Ile—Glu(γOR)—Gly—Arg—pNA |
|           | cbo-D—Arg—Gly—Arg—pNA |
| Factor XIa | Glu—Pro—Arg—pNA |
| Plasmin | (D/L)—Val—Leu—Lys—pNA |
|         | D—Val—Phe—Lys—pNA |
|         | Ts—Gly—Pro—Lys—pNA |
|         | Glu—Phe—Lys—pNA |
| Urokinase | Glu—Gly—Arg—pNA |
|           | Bz—Ala—Gly—Arg—pNA |
| tPA | (D/L)—Ile—Pro—Arg—pNA |
| C1-esterase | z-Val—Gly—Arg—pNA |
| Kallikrein | (D/Bz)—Pro—Phe—Arg—pNA |
| Neutrophile elastase | Glu—Pro—Val—pNA |
|                      | Ala—Ala—Pro—Val—pNA |
| Cathepsin G | Ala—Ala—Pro—Phe—pNA |
|             | Ala—Ala—Pro—Leu—pNA |
| Pancreatic elastase | Ala—Ala—Ala—pNA |

Other substrate sequences can be determined by determining the best artificial small molecule peptide substrates (i.e. Ala-Ala-Pro-Phe-pNA) as determined by $k_{cat}$ and $k\mu$, or by examining the sequence of natural protein substrates (e.g. fibrinogen for thrombin).

After determining the amino acid sequence which a protease will bind to (i.e. its specific substrate sequence), that sequence is used to replace all or a portion of the active site of PN-1. The PN-1 variant having the substrate-binding sequence will then competitively bind the substrate of the protease, thereby inhibiting the action of the protease. Examples of PN-1 variants having a sequence for binding the substrate of a protease are as follows:

23

TABLE 8

| Record # | NCY | mutation | sequence | indication |
|---|---|---|---|---|
| 1 | NCY2301 | XaS | IEGR - - | anticoag. |
| 2 | NCY2302 | Fibrinogen | DPLAGGGGVR - - | thrombin inhibition |
| 3 | NCY2303 | HMWK | SPFR - SVQ | kallikrein inh. |
| 4 | NCY2310 | FPR | FPR - - | thrombin |
| 5 | NCY2311 | EPV | EPV - - | elastase |
| 6 | NCY2321 | AAPF | AAPF | cathepsin G. inh. |
| 7 | NCY2322 | AAPL | AAPL - - | Elastase |
| 8 | NCY2323 | AAPV | AAPV - - | Elastase |
| 9 | NCY2324 | AAPI | AAPI - - | Elastase |

The activity of PN-1 variants having substrate binding sequences is tested by determining the second-order association rate constants for the binding of each variant against a panel of protease substrates.

PN-1 Chimeras

An example of a PN-1 chimeric protein An example of producing a chimeric protein is as follows. In general a chimeric protein can be produced from, for example, a first protein, which has virtually no binding affinity with respect to a given receptor, and a second protein, which might have very high binding affinity with respect to that receptor. (A receptor can be any protein or a portion thereof, ligand, cell surface area or molecule.) By attaching the binding region of the second protein to the first protein one can provide a chimeric protein with the biochemical functions of the first protein which will bind to the receptor previously bound only by the second protein.

Chimeric proteins of PN-1 can be produced by fusing all or a fragment of another protein to PN-1. Preferably, the amino terminal fragment of a protein such as urokinase is fused to PN-1 in order to localize PN-1 to a different receptor, i.e. to the urokinase receptor. In addition to using urokinase, it is possible to fuse the amino terminal fragment of proteins such as tPA, Factor IX, Factor X, and Protein C. Examples of PN-I chimeras are as follows:

TABLE 9

| Record # | NCY | mutation | sequence | indication |
|---|---|---|---|---|
| 1 | NCY2501 | ATF-PN1 | urokinaseATF | anti-metastasis |
| 2 | NCY2502 | HSA-PN1 | HSA chimera | long half-life |
| 3 | NCY2503 | IgG-PN1 | IgG chimera | long half-life |
| 4 | NCY2504 | F9-PN1 | Factor IX chimera | anti-coagulation |
| 5 | NCY2505 | F10-PN1 | Factor X chimera | anti-coagulation |
| 6 | NCY2506 | APC-PN1 | Protein C chimera | pro-coagulant |

Chimeric proteins such as those exemplified above can be produced by genetic engineering (e.g. by manipulation of DNA to provide a fusion protein) using skills well known in the art. However, PN-1 chimeras are preferably produced by chemically fusing an N-terminal fragment of a different protein to the PN-1. For example, a PN-1 chimera can be produced by chemical linkage of purified preparations of both protein components. Such linkage is conveniently accomplished by using bi-functional cross-linking reagents. Methods for chemically establishing such linkages are well known to those skilled in the art. Specific chimeras which might be produced in this manner include those produced by fusing PN-1 to any one of: EGF; Factor IX; Factor X; and APC.

24

The activity of PN-1 chimeras is treated by screening the chimera against a panel of proteases and determining the second-order rate association constant as described above. The activity of one PN-1 chimera is provided below:

TABLE 10

2501 (ATF-PN-1)

| Protease | Second Order Rate Constant ($M^{-1}S^{-1}$) |
|---|---|
| 1) Thrombin | $5.8 \times 10^5$ |
| 2) Plasmin | $3.5 \times 10^5$ |
| 3) Plasmin (hp) | — |
| 4) Xa | — |
| 5) Xa (hp) | — |
| 6) Urokinase | $2.3 \times 10^5$ |
| 7) Urokinase (hp) | — |
| 8) Kallikrein | — |
| 9) Cathepsin G | — |
| 10) Activated protein C | — |
| 11) Activated protein C (hp) | — |
| 12) Elastase | — |

(hp) indicates in the presence of 10 µg/ml of heparin.

Use and Administration

The different cysteine-PEGylated proteins of the invention (as indicated above) can provide different effects and pharmaceutical compositions. One of the uses of the cysteine-PEGylated proteins of the invention is the inclusion of such within various topical formulations such as creams or gels, or a combination of such formulations, with various bandages for application to, for example, wounds to aid in wound healing and decrease inflammation at wound sites. For example, as cysteine-PEGylated versions of PN-I, and particular PN-I variants and PN-I chimeric proteins, have activity useful in reduction of inflammation, injectable formulations containing these proteins of the invention may be injected directly into inflamed joints or other inflamed areas of the body in order to decrease the inflammation. Further the formulations of the invention may be used prophylactically by providing the cysteine-PEGylated versions of these proteins to a particular site which may be subjected to trauma, (such as in surgery), and thus inflammation, to prevent the inflammation from occurring.

It is pointed out that PN-1 is not found in significant quantities in plasma and may function primarily in tissues. The high affinity heparin binding site of PN-1 appears to serve to localize PN-1 to connective tissues and cells which contain sulfated proteoglycans on their surface and surrounding extracellular matrix. Thus, the primary role of PN-1 seems to be in regulating proteolytic activity in tissues as opposed to blood. In that PN-1 is found in brain tissue another aspect of the invention involves delivering formulations of the invention containing PN-1 variants or chimeric proteins in order to facilitate peripheral or central nerve regeneration. Formulations, routes of administration and dosages for use of PN-1 in the treatment of inflammation and wounds are described in U.S. Pat. Nos. 5,206,017; 5,196,196; and 5,112,608; each of which are incorporated herein by reference to the extent that such methods of treatment using PN-1 are described.

Generally, the pharmaceutical compositions containing the cysteine-PEGylated proteins of the invention will be formulated in a non-toxic, inert, pharmaceutically acceptable aqueous carrier medium, preferably at a pH of about 5 to 8, more preferably 6 to 8, although the preferred pH of the pharmaceutical composition may vary according to the protein employed and condition to be treated.

PEGylated proteins are ready for immediate therapeutic use (i.e., do not require reconstitution), have increased solubility and have an increased half-life and are reduced in immunogenicity and antigenicity relative to the unmodified protein (Nucci et al. 1991 *Adv. Drug Delivery res.* 6:133–151). The increased half-life of PEGylated proteins decreases the amount of protein needed for an effective dosage, reduces the number and frequency of administrations required, and decreases the patient's exposure to the protein, thus decreasing the potential for allergic reactions, toxic effects, or other side effect. These characteristics of PEGylated proteins allow for long-term use of the protein with less potential for undesirable side effects related to protein immunogenicity and/or toxicity. Exemplary proteins for which an increase half-life has been accomplished by PEGylation of the protein include: hGH, insulin, interferon-alpha2A (IFN-alpha-2A), interferon-alpha2B (IFN-alpha-2B), tPA, EPO, G-CSF, antigen E, arginase, asparaginase, adenosine deaminase, batroxobin, bovine serum albumin, catalase, elastase, factor VIII, galactosidase, alpha-galactosidase, beta-glucuronidase, IgG, honeybee venom, hemoglobin, interleukin-2, lipase, phenylalanine ammonia lyase, alpha$_1$-proteinase inhibitor, pro-urokinase, purine nucleoside phosphorylase, ragweed allergen, streptokinase, superoxide dismutase, tPA, D-alpha-tocopherol, trypsin, tryptophanase, uricase, and urokinase (see in general Nucci et al. ibid.; see also Davis et al. 1981 *Clin. Exp. Immunol.* 46:649–652 (bovine adenosine deaminase); Nishimura, et al. 1985 *Life Sci.* 33:1467–1473 (batroxobin); Savoca et al. 1979 *Biochimica et Biophysica ACTA* 578:47–53 (arginase); Till, et al. 1983 *J. Trauma* 23:269–277 (asparaginase); Veronese, et al. 1983 *J. Pharm. Pharmacol.* 35:281–283 (superoxide dismutase); Davis et al. 1981 *Lancet* 2:281–283 (urate oxidase); and Dellinger et al. 1976 *Cancer* 38:1843–1846). Several PEGylated proteins have already been approved for use by the U.S. Food and Drug Administration (FDA). These PEGylated proteins include: hGH, insulin, interferon-alpha2A, interferon-alpha2B, tPA, EPO, G-CSF, and a hepatitis B vaccine which contains PEGylated proteins (Nucci et al. ibid).

PEGylated proteins may be administered for the treatment of a wide variety of diseases. Exemplary disease conditions and the proteins useful in treatment of these diseases are provided in Table 11.

TABLE 11

| Exemplary Disease Conditions Amenable to Protein Therapy | |
|---|---|
| Enzyme Deficiency | Endotoxic Shock/Sepsis |
| adenoeine deaminase$_1$ | Bactericidal/permeability |
| Purine nucleotide | increasing protein |
| phosphorylase | Lipid-binding protein (LBP) |
| Galactosidase | |
| β-glucuronidase | |
| Antioxidants for Cancer Therapy | Blood Protein Replacement |
| Superoxide dismutase | Therapy |
| Catalase | Hemoglobin |
|  | Albumin |
| Cancer | Growth Factors (for use in wound |
| Interferon-α | healing, induction of red blood |
| Interferon-γ | cell formation, etc.) |
| IL1-α | Epidermal growth factor |
| Phenylalanine ammonia lyase | G-CSF |
| Arginase | Interferon-γ |
| L-asparaginase | Transforming growth factor |
| Uricase | EPO |
| Granulocyte colony | Thrombopoietin |

TABLE 11-continued

| Exemplary Disease Conditions Amenable to Protein Therapy | |
|---|---|
| stimulating factor (GCSF) | Insulin-like growth factor-1 |
| Monoclonal antibodies | Insulin |
| Tissue necrosis factor | hGH |
| Cardiovascular Disease | |
| Tissue Plasminogen Activator | |
| Streptokinase (native or chimeric) | |
| Urokinase (native or chimeric) | |
| α-antitrypsin | |
| antithrombin-III | |
| Other proteaese or protease inhibitors | |
| Apolipoptoreins (particularly B-48) | |
| Circulating Scavenger Receptor APO Al$_2$ | |

$_1$For treatment of severe combined immunodeficiency
$_2$Converts low-density lipoproteins to high-density lipoproteins Cysteine-PEGylated proteins may be delivered within the formulations and by the routes of administration discussed above. The particular formulation, exact dosage, and route of administration will be determined by the attending physician and will vary according to each specific situation. Such determinations are made by considering such variables as the condition to be treated, the protein to be administered, the pharmacokinetic profile of the particular protein, as well as various factors which may modify the effectiveness of the protein as a drug, such as disease state (e.g. severity) of the patient, age, weight, gender, diet, time of administration, drug combination, reaction sensitivities, tolerance to therapy, and response to therapy. Long-acting protein drugs might only be administered every 3 to 4 days, every week or once every two weeks. Where cysteine-PEGylated proteins are used in the pharmaceutical composition, the clearance rate (i.e. the half-life of the protein) can be varied to give ultimate flexibility to fit the particular need of the patient by changing, for example, the number of PEG moieties on the cysteine-protein, the size of the PEG moiety.

It is generally not possible to obtain desirable results by administering large protein compounds by oral delivery systems. Such proteins are generally digested in the GI tract (unless formulated with special carriers) and do not enter the cardiovascular system in their original forms due to such digestion. The cysteine-PEGylated proteins of the invention can be administered by any type of injection, such as intramuscular or intravenous, thus avoiding the GI tract. Other modes of administration include transdermal and transmucosal administrations provided by patches and/or topical cream compositions. Transmucosal administrations can include nasal spray formulations which include the cysteine-PEGylated proteins of the invention within a nasal formulation which contacts the nasal membranes and diffuses through those membranes directly into the cardiovascular system. Cysteine-PEGylated proteins may have an increased ability to cross membranes and thus may enter the body more easily. Formulations which include the cysteine-PEGylated proteins of the invention within aerosols for intrapulmonary delivery are also contemplated by this invention, as are intraocular delivery systems wherein the cysteine-PEGylated proteins are included within ophthalmic formulations for delivery in the form of eye drops.

Where cysteine-PEGylated proteins are employed, the daily regimen should generally be in the range of the dosage for the natural, recombinant, or PEGylated protein. Normal dosage amounts may vary from 0.1 to 100 micrograms, up to a total dose of about 1 g, depending upon the route of administration. Guidance as to particular dosages for particular proteins is provided in the literature with respect to the administration of either native proteins and/or proteins PEGylated by conventional methodologies. For example, guidance for administration of antithrombin-III for the prevention of fibrin clot formation may be found in U.S. Pat. Nos. 5,292,724 and 5,182,259; guidance for administration of human growth hormone (hGH) in the treatment of individuals intoxicated with poisonous substances may be found in U.S. Pat. Nos. 5,140,008 and 4,816,439; guidance for administration of hGH in the treatment of topical ulcers may be found in U.S. Pat. No. 5,006,509; guidance for administration of (EPO) for treatment of anemia and pulmonary administration of EPO may be found in U.S. Pat. No. 5,354,934; guidance for administration of EPO, GM-CSF, G-CSF, and multi-CSF for treatment of pancytopenia may be found in U.S. Pat. No. 5,198,417; guidance for administration of EPO for treating iron overload may be found in U.S. Pat. No. 5,013,718; guidance for administration of EPO in the treatment of hemoglobinopathies may be found in U.S. Pat. No. 4,965,251; guidance for administration of insulin the treatment of diabetes may be found in U.S. Pat. No. 4,478,822; guidance for delivery of asparaginase for treatment of neoplasms may be found in U.S. Pat. Nos. 4,478,822 and 4,474,752; guidance for administration of L-asparaginase in the treatment of tumors is found in U.S. Pat. No. 5,290,773; guidance for administration of prostaglandin E1, prostaglandin E2, prostaglandin F2 alpha, prostaglandin I2, pepsin, pancreatin, rennin, papain, trypsin, pancrelipase, chymopapain, bromelain, chymotrypsin, streptokinase, urokinase, tissue plasminogen activator, fibrinolysin, deoxyribonuclease, sutilains, collagenase, asparaginase, or heparin in a cryogel bandage for treatment of sites of trauma may be found in U.S. Pat. No. 5,260,066; guidance for the administration of superoxide dismutase, glucocerebrosides, asparaginase, adenosine deaminase, interferons (alpha, beta, and gamma), interleukin (1,2,3,4, 5,6,7), tissue necrosis factor (TNF-alpha or TNF-beta), and colony stimulating factors (CSF, G-CSF, GM-CSF) in liposomes may be found in U.S. Pat. No. 5,225,212; guidance for administration of asparaginase or insulin in the treatment of neoplastic lesions may be found in U.S. Pat. No. 4,978,332; guidance for administration of asparaginase in the reduction of tumor growth may be found in U.S. Pat. No. 4,863,910; guidance for the administration of antibodies in the prevention of transplant rejection may be found in U.S. Pat. Nos. 4,657,760 and 5,654,210; guidance for the administration of interleukin-1 as a therapy for immunomodulatory conditions including T cell mutagenesis, induction of cytotoxic T cells, augmentation of natural killer cell activity, induction of interferon-gamma, restoration or enhancement of cellular immunity, and augmentation of cell-mediated anti-tumor activity may be found in U.S. Pat. No. 5,206,344; guidance for the administration of interleukin-2 in the treatment of tumors may be found in U.S. Pat. No. 4,690,915; and guidance for administration of interleukin-3 in the stimulation of hematopoiesis, as a cancer chemotherapy, and in the treatment of immune disorders may be found in U.S. Pat. No. 5,166,322.

All U.S. patents cited hereinabove are incorporated herein by reference with respect to the guidance provided in administration of the particular protein and/or PEGylated protein described therein.

Any of the above suggested means of administration could be provided in a variety of different formulations. The formulations can be designed to provide the cysteine-PEGylated proteins systemically or to a particular site. Further, the formulations can be designed so as to provide the cysteine-PEGylated proteins as quickly as possible or in a sustained release or timed released manner. For example, topical formulations could be created whereby the cysteine-PEGylated proteins of the invention were incorporated or disbursed throughout topical polymer formulations capable of slowly releasing the cysteine-PEGylated proteins to a wound site in order to continually aid in wound healing and in preventing inflammation. In addition, formulation containing the cysteine-PEGylated proteins of the invention may also contain other reactive components (e.g., antimicrobials, anti-inflammatory agents) which can act synergistically with the cysteine-PEGylated protein. The formulations may also include other inert components such as surface-wetting agents, defoaming agents, agents to aid in translocation of the cysteine-PEGylated protein across, for example, the epithelial barrier, etc.

As indicated above, different formulations of the invention can be administered in a variety of different manners in order to introduce the cysteine-PEGylated proteins into the cardiovascular system. The cysteine-PEGylated proteins are administered for a variety of purposes which generally relate to, for example: blocking proteolytic activity; inhibition of tumor growth or metastasis; promotion of wound healing and/or nerve fiber regeneration; replacement therapy for protein-deficient states (e.g. diabetes); inhibition of bacterial, fungal, or viral growth; enhancement of the immune response; induction of maturation of bone marrow stem cells (e.g. in bone marrow transfers); regulation of blood clotting; treatment of inflammation; or treatment of bacterial sepsis and endotoxic shock; replacement of albumin or hemoglobin (e.g. to replace blood transfusions). In particular, intravenous formulations containing the cysteine-PEGylated versions of PN-I, PN-I variants, or PN-I chimeric proteins are useful for their anti-thrombolytic effect and therefore can be administered to aid and a prevention and/or alleviation of strokes and/or heart attacks.

EXAMPLES

The following examples are provided so as to give those of ordinary skill in the art a complete disclosure and description of how to make and use the PN-1 variants of the invention and are not intended to limit the scope of what the inventors regard as their invention. Efforts have been made to insure accuracy with respect to the specifics given such as the association rate constants and temperature but some experimental errors and deviations should be accounted for. With respect to the formulation examples, parts are parts by weight, and any temperature readings are in degrees centigrade and all experiments were carried out at or near atmospheric pressure.

EXAMPLE A

The Synthesis of PN-1

PN-1 was purified to homogeneity from serum-free medium conditioned by human foreskin fibroblasts in microcarrier cultures by affinity chromatography on heparin-agarose, followed by gel exclusion chromatography, as described in detail by Scott, R. W. et al., *J. Biol. Chem.* (1985) 260:7029–7034, incorporated herein by reference. Of course, other chromatographic supports which contain heparin for affinity binding or other matrix such as cm sepharose or S-sepharose can also be used. The purified protein shows an $M_r$ of 42–43 kd, based on sedimentation equilibrium analysis, or of 47 kd, estimated from gel-exclusion chromatography. The purified material shows the properties exhibited by PN-1 when contained in conditioned medium, including formation of sodium dodecylsulfate-stable complexes with thrombin, urokinase, and plasmin; inhibition of protease activity; heparin-enhanced inhibition of thrombin; and cellular binding of protease-PN complexes in a heparin-sensitive reaction. The N-terminal amino acid sequence of the isolated, purified protease nexin was determined for the first 34 amino acids to be: Ser-His-Phe-Asn-Pro-Leu-Ser-Leu-Glu-Glu-Leu-Gly-Ser-Asn-Thr-Gly-Ile-Gln-Val-Phe-Asn-Gln-I le-Val-Lys-Ser-Arg-Pro-His-Asp-Asn-Ile-Val-Ile.

The PN-1 variants of the present invention can be synthesized by utilizing the pure PN-1 which has been isolated and purified in the manner indicated above. The variants can be obtained by cleaving the purified PN-1 protein at the $P_1$ or $P_1'$ site and replacing the arginine, serine or both residues at that site with the desired non-polar substitute residue. After replacement of the desired residue with the desired non-polar residue, the segments can be fused utilizing protocols known to those skilled in the art. Although such methodology could be utilized in order to obtain the variants of the present invention, this methodology is somewhat cumbersome and is extremely limited, due to the very small amounts of PN-1 which can be extracted and purified. Accordingly, although the above procedure could be utilized, it is not the preferred method of making PN-1 or the variants disclosed herein. PN-1 and its variants are generally produced utilizing recombinant technology, as described below.

EXAMPLE B
A Generalized Recombinant Synthesis of PN-1

Methods of producing protease nexin-1 utilizing recombinant technology are disclosed within published European patent application 873049126 which published application is incorporated herein by reference to disclose recombinant technologies utilized in producing protease nexin-1. The procedure can be modified by those skilled in the art, reading this disclosure, to obtain PN-1 variants.

cDNA encoding the complete human PN-1 protein was obtained from a foreskin fibroblast DNA library. The retrieval of this clone took advantage of probes based on the amino acid sequence determined in the native protein. The cloned cDNA is amenable to expression in recombinant cells of both procaryotic and eucaryotic organisms by excising the coding sequence from the carrier vector and ligating it into suitable expression systems.

The PN-1 can be directly produced as a mature protein preceded by a Met N-terminal amino acid (which may or may not be processed, depending on the choice of expression systems) may be produced as a fusion protein to any desirable additional N-terminal or C-terminal sequence, or may be secreted as a mature protein when preceded by a signal sequence, either its own, or a heterologous sequence provided by, for example, the known signal sequence associated with the bacterial-lactamase gene or with secreted human genes such as insulin or growth hormones. Means for providing suitable restriction sites at appropriate locations with respect to the desired coding sequence by site-directed mutagenesis are well understood, and the coding sequence can thus be provided with suitable sites for attachment to signal sequence or fusion sequence, or into expression vectors.

If bacterial hosts are chosen, it is likely that the protein will be produced in nonglycosylated form. If the PN-1 is produced intracellularly as a "mature" protein, the N-terminal methionine may be only partially processed, or not processed at all. Thus, the protein produced may include the N-terminal Met. Modification of the protein produced either intracellularly or as secreted from such bacterial host can be done by providing the polysaccharide substances, by refolding using techniques to sever and reform disulfide bonds, or other post-translational ex vivo processing techniques. If the protein is produced in mammalian or other eucaryotic hosts, the cellular environment is such that post-translational processing can occur in vivo, and a glycosylated form of the protein is most likely produced.

The recombinant cells are cultured under conditions suitable for the host in question, and the protein is recovered from the cellular lysate or from the medium, as determined by mode of expression. Purification of the protein can be achieved using methods similar to that disclosed by Scott, R. W. et al., *J. Biol. Chem.* (supra), or by other means known in the art.

Once DNA segments coding for the production of PN-1 have been inserted into bacterial hosts, multiple copies of the segments can, of course, be cloned by growing the bacteria. The segments can be extracted from the bacteria by the use of conventional methodology whereby the DNA is extracted by subjecting disrupted cells to centrifugation and then subjecting the extracted DNA to enzyme digestion, which will result in obtaining the desired segments by subjecting the digested DNA to separation processes such as gel electrophoresis and blotting. The segments coding for the production of PN-1 can then be subjected to conventional recombinant methodologies in order to substitute codons coding for the arginine and/or serine with new codons which code for the production of the desired non-polar amino acid residue. Once such recombinant segments are produced, they can be reinserted into vectors and hosts in the manner described above in order to obtain the production of the desired PN-1 variants. A variety of vector and host systems known to those skilled in the art can be used.

In addition, it is pointed out that PN-1 variants might be made by using recombinantly produced PN-1 and then substituting only the desired "R" group (e.g., —OH of serine 346) with a non-polar "R" group (e.g., —CH$_2$CH$_2$—s—CH$_3$) to get a PN-Met$_{346}$ variant. Such replacements of the "R" group can be carried out using published protocols known to those skilled in the art.

EXAMPLE C
Production of Recombinant PN-1 Variants in Insect Cells Using a Baculovirus Expression System C.1. Construction of plasmid expression vector:

In order to produce PN-1 and/or PN-1 variants in insect cells, the cDNA sequence must first be inserted into a suitable plasmid expression vector, such as pAC373. Appropriate restriction sites for this insertion can be created by standard site-directed mutagenesis procedures. The essential properties of a suitable expression vector include a transcriptional promoter such as the polyhedron gene promoter of pAC373, and flanking homologous sequences to direct recombination into the baculovirus genome. A polyadenylation signal, such as the one from the polyhedron gene present in this plasmid vector, may or may not be necessary for expression of the recombinant gene. A marker gene such as the β-galactosidase gene of *E. coli*, juxtaposed to regulatory sequences including a transcriptional promoter and possibly a polyadenylation signal, may be included in the vector but is not essential for expression of a convected gene.

C.2. Creation of recombinant baculovirus:

A chimeric baculovirus is created by homologous recombination between the expression plasmid containing the PN-1 target gene and wild type baculovirus DNA. Plasmid and wild type baculovirus DNA are co-precipitated by the calcium phosphate technique and added to uninfected *Spodoptera frugiperda* (Sf9) insect cells. Four to seven days following transfection, cells will exhibit a cytopathic morphology and contain the nuclear occlusion bodies typically produced by viral infection. The cell-free culture media containing both wild type and recombinant virus is harvested.

C.3. Identification and isolation of chimeric baculovirus:

Clonal isolates of virus can be obtained from this co-transfection stock by plaque purification on Sf9 cell monolayers overlaid with agarose. Candidate plaques for analysis will be identified by a plaque morphology negative for occlusion bodies. If the expression plasmid contains a marker gene such as β-galactosidase, recombinant plaques will be indicated by the blue color produced from a chromogenic substrate such as 5-bromo-4-chloryl-3-indolyl-b-D-galactopyranoside (X-gal) in the agarose plating medium. Picked plaques will be used for inoculation of cells in multiwell dishes. The resulting cell lysates and infected cell supernatants can be evaluated for expression of recombinant PN-1, using standard activity or immunological assays. Positive wells may require additional rounds of plaque purification to obtain pure recombinant virus stocks free from wild type contamination.

C.4. Batch production of PN-1:

Sf9 cells are adapted to growth in serum-free, low protein medium such as ExCell (J. R. Scientific). Cells are collected from suspension culture by gentle centrifugation and resuspended in fresh medium containing the viral inoculum at a concentration of ten million cells per ml., using a multiplicity of infection of one virus plaque forming unit per cell. After a period of two hours, the culture is diluted five fold with fresh medium and incubated two to three days. At the end of that time, the cells are pelleted by centrifugation and the conditioned medium harvested. PN-1 is purified from the cell-free supernatant by standard means.

Variants of PN-1 may be created and produced in the same manner as described above.

C.5. Characterization of insect cell derived PN-1:

PN-1 produced in insect cells using a baculovirus expression system is a glycosylated protein of approximate molecular weight of 42,000 kd. The N-terminal amino acid sequence is identical to that of mature mammalian cell PN-1, indicating correct processing of the signal sequence. The specific activity vs thrombin and association kinetics, including rate enhancement effect of heparin, are indistinguishable from authentic PN-1.

EXAMPLE D

Production of Recombinant PN-1 Variants in *E. coli* in Inclusion Bodies or in Soluble Form D.1 Cloning of PN-1

The cloning of PN-1 and expression has been described (McGrogan, et al., (1988) Bio/Technology). The gene for PN-1 was generated by PCR from the CHO expression vector using the following oligonucleotides:

PNPCR-forward 5' TG.GAA.GGA.CAT.ATG.AAC.TG-G.CAT.CTC

PNPCR-reverse 5' TCT.TTT.GTA.TAC.TGA.T-CA.GGG.TTT.GT generating an NdeI and BclI site, respectively. The resulting fragment was cut with NdeI and BclI and subcloned into pGEMEX-1 vector (Promega).

The pGEMEX *E. coli* expression vector contains three RNA polymerase promoters. The T7 promoter is positioned upstream from the gene 10 leader fragment.

We removed the gene 10 region from pGEMEX, but retained the T7 RNA polymerase binding site and NdeI and BamHI cloning sites. To accomplish this the NdeI site at 3251 in pGEMEX was removed by partial NdeI digest followed by Klenow fill-in and relegation. This plasmid is referred to as pT7-NK. pT7-NK was cut with NdeI and BamHI to remove the gene 10 fusion protein region. The linear vector was isolated and ligated with the PCR-generated PN-1 linear fragment, cut with NdeI and BclI, described above. This plasmid is referred to as pT7PN-1. The correct sequence was confirmed by sequencing the entire coding region for PN-1.

The native signal sequence was removed using PCR and the following oligos:

PCRMET.forward 5'GAT.ATA.CAT.ATG.TCC.CAC.T-TC.AAT.CCT.CTG

PCRMET.reverse 5'GGG.GGC.ACT.TGT.CGA.CCC.A-CA.CCG.GAA with an NdeI and SalI site, respectively. This generated a 690 base pair fragment which could replace the native signal and a portion of the amino terminus of PN-1 with a start codon (Met) and the amino terminus of PN-1. Again, the correct sequence was confirmed by sequencing. The expression of the resulting protein is expected to be intracellular, either in inclusion bodies or as soluble protein.

D.2. Mutagenesis of PN-1

The plasmid pT7PN1 has an F1 ori for the production of single-stranded DNA. Thus pT7PN1 was transformed into the *E. coli* strain CJ236 for the production of ssDNA to be used as a template for site-directed mutagenesis according to the method of Kunkel (Kunkel, T. A. (1988) in Nucleic Acids and Molecular Biology (Eckstein, F., Lilley, D. M. J. Eds.) Vol. 2, p. 124, Springer-Verlag, Berlin and Heidelberg).

The general rationale for mutant generation is based upon four general methods.

In the first method, single amino acid substitutions in the region of P4 to P4' are generated by site directed mutagenesis. In general, substitutions at the P1 site will have the most dramatic effects. However, substitutions at other residues within the active site region will give changes in association rate constants with serine proteases.

In the second method, sequences found at the active site region of other serpins were grafted onto PN-1. A number of combinations must be created to determine how much of the sequence at the active site must be changed to change the specificity and kinetics. The $P_4$ to $P_4'$ region is generally found to be most important, but amino acids residues outside this region can have pronounced affects on protease inhibition.

In the third method, sequences which have been found to be particularly good substrates are added to or used to replace a sequence of PN-1. Prior to making these mutants, it was not clear if these changes would ruin the inhibitory effects of PN-1 and turn PN-1 from an inhibitor of proteolysis into a substrate. In fact, incorporation of Ala-Ala-Pro-Phe, a good substrate sequence for subtilisin, into PN-1 results in a molecule which is cleaved particularly well by subtilisin. However, PN-1 variants have now been obtained which are good inhibitors of mammalian serine proteases based upon this approach.

In the fourth method, optimum inhibitor sequences can be generated by using a phage display system. Since PN-1 forms covalent interactions with the target protease, it is important that one is not selecting for mutants which bind more tightly than the parent PN-1 molecule. Rather, one selects for PN-1 variants which bind more rapidly to the target protease by allowing phage-displayed variant PN-1 library to interact with the immobilized target protease for only short times. Thus, only rapid-binding variants will be selected. This is a novel application of the phage display system.

The following oligonucleotides were used to generate a mutant specific for the protease shown at the end of the sequence:

5'GCA.ATT.CTC.ATT.GCA.NN(G/C).TCA.TCG. CCT.CCC [R345I, R345M, R345L, R345V] (elastase), R345K (plasmin), R345D, R345E 5'ATT.CTC.ATT.GCA.GTG.AGC.TCG.CCT.CCC.TG R345V (elastase)

5'ATT.CTC.ATT.GCA.AGA.ATA.TCG.CCT.CCC.TGG S3461 (Factor Xa)

5'ATT.CTC.ATT.GCA.AGA.ACA.TCG.CCT.CCC.TCC S346T (Factor Xa, C1-esterase)

5'ACA.ACT.GCA.ATT.CTG.GCT.GGA.AGA.TCA.T-TG.AAT.CCC.TGG.            TTT.ATA I343A;A344G;S347L;P348N (ATIII-like, thrombin, Factor Xa)

5'ACA.ACT.GCA.ATT.CTC.TTT.CCA.AGA.T-CA.TCG.CCT.CCC I343F;A344P (FPR, thrombin)

5'ACT.GCA.ATT.CTC.ATT.CCA.TTA.TCA.TCG.CAG. GTC.CGG.TTT.           ATA.GTA.GAC A344P;R345L;P348Q;P349V;W350R (HCII-like)

5'GAA.GAT.GGA.ACC.AAA.GCT.TCA.GAC.TTT.TTG. GCT.GAA.GGT. GGC.GGT.GTA.AGA.TCA.TCG.C-CT.CCC.TGG A336D;A337F; T338L;T339A;A340E;I341G;L342G;A344V (fibrinogen-like, thrombin)

5'GCA.ACA.ACT.GCA.ATT.ATC.GAG.GGA.AGA.T-CA.TCG.CCT L342I;I343E;A344G (Factor Xa)

5'ACA.ACT.GCA.ATT.CTC.GAG.CCA.GTA.T-CA.TCG.CCT.CCC I343E;A344P;R345V (elastase, cathepsin G)

5'ACT.GCA.ATT.CTC.ATT.GGA.AGA.TCA.TCG.CCT A344G (faster kinetics)

5'ACT.GCA.ATT.CTC.ATT.CCA.AGA.TCA.TCG.CCT A344P (faster kinetics)

5'GCA.ACA.ACT.GCA.ATT.AGC.CCT.TTC.AGA.T-CA.GTG.CAG.CCC

TGG.TTT.ATA L342S;I343P;A344F;S347V;P348Q (high molecular weight kininogen-like; kallikrein)

5'GCA.ACA.ACT.GCA.ATT.GCC.GCT.CCA.TTC.T-CA.TTG.CCT.CCC.

TGG.TTT L342A;I343A;A344P;R345F (cathepsin G)

5'GCA.ACA.ACT.GCA.ATT.GCC.GCT.CCA.GTA.T-CA.TCG.CCT.CCC.

TGG.TTT L342A;I343A;A344P;R345L (elastase)

5'GCA.ACA.ACT.GCA.ATT.GCC.GCT.CCA.CTA.T-CA.TCG.CCT.CCC.

TGG.TTT L342A;I343A;A344P;R345L (elastase)

5'GCA.ACA.ACT.GCA.ATT.GCC.GCT.CCA.ATA.T-CA.TCG.CCT.CCC.

TGG.TTT L342A;I343A;A344P;R345I (elastase)

D.3. Expression and Purification of Protease Nexin Variants in *E. coli*

JM109 (DE3) contains a chromosomal copy of the gene which codes for T7 RNA polymerase under the control of the inducible lac promoter. JM109 (DE3) containing pT7PN-1 (or a variant of PN-1) was grown overnight in 2xYT+0.2% glucose+100 mg/ml carbenicillin at 28°–32° C. Low temperature and high nutrient containing solution is helpful in generating productive innoculants. The inoculum was diluted 1:250 to 1:500 and grown to $OD_{600}$~1 in a shake flask or ~50 in a fermentor at 26°–37° C., and induced with IPTG at 0.1–1.0 mM for 4–16 hours. The bacteria were collected by centrifugation, resuspended in 10 mM TRIS, pH 8, 1 mM EDTA, and disrupted by high pressure homogenization. Inclusion bodies were collected by centrifugation, washed with 1M NaCl, 0.05% triethylamine, and the protein refolded from a 6M guanidine solution by rapid dilution. PN-1 was purified by capture on FastS sepharose and eluted with 0.6M NaCl, diluted to 0.25M NaCl and passed over FastQ sepharose to remove endotoxin and recaptured on FastS sepharose and eluted with 0.6M NaCl or a gradient of 0.25 to 1M NaCl.

Alternatively, PN-1 can be generated in a soluble form within *E. coli* by adjusting the fermentation conditions. This procedure provides a greater yield of soluble PN-1 as the fermentation temperature is decreased from 37° C. to 26° C. with a concomitant loss in inclusion body material. This is quite an unexpected finding, since PN-1 is bactericidal when native PN-1 is added to *E. coli*. To purify soluble PN-1, the cell supernatant from the disruption step was clarified by centrifugation and filtration or by treatment with polycations such as polyethyleneimine or Biacryl™ followed by centrifugation and filtration, and the soluble protein was purified as above. The generation of soluble material has many advantages: there is more certainty that the protein is correctly folded, there are no refolding steps, there is greater reproducibility from batch to batch.

The production of PN-1 was about 50 mg per gram of cell paste. This corresponds to about 50 mg per liter of production at a cell density of 1 $OD_{600}$ or up to 2.5 grams of soluble PN-1 per liter of fermentation. This represents a substantial advance in the state of the art of PN-1 production.

D.4. Activity assay for PN-1 Variants

Refolded or soluble protein was tested for capacity to inhibit thrombin in a standard assay. Briefly, serial 2-fold dilutions of PN-1 variant were added to microtiter plate wells (50 µl/well), followed by 50 µl of a 30 µg/ml heparin solution, followed by 1 NIH unit of thrombin in 50 µl. These were allowed to incubate at 25° C. for 15 minutes. Residual thrombin activity was measured by the addition of 50 µl S-2238 (Kabi Pharmaceuticals) at 0.625 mg/ml. PN-1 variants were tested for their ability to inhibit urokinase using the substrate S-2444, plasmin using the substrate S-2390, tPA using the substrate S2288, Factor Xa using the substrate S-2222 or S-2765, kallikrein using the substrate S-2302, human neutrophil elastase using s-AAPV-pna (Sigma), cathepsin G using s-AAPF-pna (Sigma) in a similar manner, with or without the addition of heparin.

The second-order rate association constants were determined for appropriate inhibitors-proteases combinations by combining equal-molar amounts of each protein (determined by titration as above) for various times from 1 second to 4 hours (as appropriate) and following the activity loss. The $t_{1/2}$ was estimated from resulting curves. The $k_{assoc}$ was estimated according to the equation $ln2/ |PN-1| \times t_{1/2}$. Alternatively, the apparent first order rate constant was determined from the slope of a plot of log (normalized activity) vs time. The second order rate constant was calculated by dividing the apparent first order rate constant by the PN-1 (or variant) concentration used.

EXAMPLE E

PN-1 Chimeras

E.1 Generation of ATF-PN1 Chimera

To generate this chimera, we first cloned the amino-terminal fragment of uPA by PCR using the oligonucleotides:

ATF.forward 5'GGT.GAT.CAT.ATG.AGC.AAT.GAA.CT-T.CAT.CAA

ATF.REVERSE 5'TTT.AGG.ACG.CGT.CTG.CGC-.CAT.CTG.CTC.AGT.CAT.G generating a NdeI and MluI site respectively. The resulting fragment was cut with NdeI and MluI and subcloned into pT7PN1 vector cut with the same enzymes to move the signal sequence. This plasmid is referred to as pT7ATF-PN1. The correct sequence was verified by automated sequencing using the T7 dye primer system (ABI).

To generate an even shorter version of ATF-PN1 which retains the urokinase receptor binding region, $ATF_{48}$-PN1 was made by introducing a MluI site (underlined) by site directed mutagenesis at codon 48 using the following oligonucleotide:

5'CAC.TGT.GAA.ATA.GAT.AAC.GCG.TAA.ACC.T-GC.TAT.GAG.

The resulting plasmid was cut with MluI to remove a 300 bp segment and ligated.

E.2 Mutagenesis of ATF-PN1

The plasmid pT7ATF-PN1 has an f1 ori for the production of single-stranded DNA. Thus pT7ATF-PN1 was transformed into the E. coli strain CJ236 for the production of ssDNA to be used as a template for site-directed mutagenesis according to the method of Kunkel (Kunkel, T. A. (1988) in *Nucleic Acids and Molecular Biology* (Eckstein, F., Lilley, D. M. J. Eds.) Vol. 2, p. 124, Springer-Verlag, Berlin and Heidelberg). In addition, PN-1 variants of interest can be subcloned into pT7ATF-PN-1 by using standard molecular biology techniques.

E.3 Expression and Purification of ATF-PN1

The resultant plasmid was transformed into the E. coli strain JM109 (DE3), grown to $OD_{600}$~1 in a shake flask or ~50 in a fermentor, and induced with IPTG at 0.1–1.0 mM for 4–16 hours at 26°–37° C. The bacteria were collected by centrifugation, resuspended in 10 mM TRIS, pH 8, 1 mM EDTA, and disrupted by high pressure homogenization. Inclusion bodies were collected by centrifugation, washed with 1M NaCl, 0.05 % TEA, and the protein refolded from a 6M guanidine solution. ATP-PN1 was purified by capture on FastS sepharose and eluted with 0.6M NaCl, diluted to 0.25M NaCl and passed over FastQ sepharose to remove endotoxin and recaptured on FastS sepharose and eluted with 0.6M NaCl or a gradient of 0.25 to 1M NaCl. Alternatively, the cell supernatant from the disruption step was clarified by centrifugation and filtration, and the soluble protein was purified as above.

E.4 Activity assay for ATF-PN1

Refolded or soluble protein was tested for capacity to inhibit thrombin in a standard assay. Briefly, serial 2-fold dilutions of ATF-PN1 were added to microtiter plate wells (50 µl/well), followed by 50 µl of a 30 µg/ml heparin solution, followed by 1 NIH unit of thrombin in 50 µl. These are allowed to incubate at 25° C. for 15 minutes. Residual thrombin activity is measured by the addition of 50 µl S-2238 (kabi Pharmaceuticals) at 0.625 mg/ml. ATF-PN1 was tested for its ability to inhibit urokinase using the substrate S-2444, or plasmin using the substrate S-2390, in a similar manner, without the addition of heparin.

Refolded or soluble protein was tested for the ability to bind to a soluble form of the urokinase receptor as measured by ELISA, or the ability to inhibit the binding of urokinase to the soluble urokinase receptor. ATF-PN1 was also tested for its ability to inhibit uPA or DFP/PMFS treated uPA binding to cells such as HT1080, U937, or THP-1 expressing uPA receptor.

EXAMPLE F

Generation of Cysteine-PEGylated Proteins

F.1 Preparation of Maleimido-PEG Reagent

Maleimido-PEG was prepared by mixing the following:
1) 100 mg methoxypolyethylene amine (20 µmol) (MW≈5,000)
2) 20 µmol γ-maleimidobutyric acid-N-hydroxy succinimide ester (GMBS)
3) 2 ml 100 mM Caps buffer, pH 10.0

The amount of the components above (particularly 1) and 2)) and the volume indicated may be varied. For example, it is permissible that the difference in the ratio of methoxy-polyethylene amine to GMBS can vary by up to ten to 100-fold. Normally, about a two-fold excess of 1) above to GMBS is preferred. While various buffers may be substituted for the Caps buffer, it is important that Tris buffers are not used in this mixture, as Tris buffers will quench the reaction. The pH of the buffer used may vary considerably, although buffers having a pH of 10.0 are preferable over buffers having a pH of 8.0. In addition, the mixture above may contain up to 50% DMSO as a cosolvent. It is particularly important that the reaction mixture does not contain a reducing agent such as dithiothreitol (DTT) or mercaptoethanol (βME).

The mixture was incubated at 37° C. for 30 minutes, although the reaction temperature may be as low as 4° C. and the reaction time may be extended for up to one hour or more. After incubation, 12 mg of Tris free base or ethanolamine was added to the mixture to quench the $NH_3$ moiety. This quenching step may be omitted.

The reacted mixture is purified by elution through a PD-10 column (G-25) (BioRad) equilibrated with 20 mM Tris (pH 7.4), 100 mM NaCl, and 0.1% Tween. The eluant was collected in 0.5 ml fractions and assayed for production of the Maleimido-PEG reagent by precipitation with 50% TCA. The resulting Maleimido-PEG (Mal-PEG) reagent is then used in to modify a selected protein by attachment of PEG to a cysteine residue(s).

F.2 Reaction of Maleimido-PEG with Protein

Prior to reaction of the protein with the Maleimido-PEG reagent, the purified protein was diluted to a concentration of about 200 pg/ml to 1 mg/ml in any suitable buffer which does not contain DTT or βME. Normally, the buffer was composed of 20 mM PIPES pH 6.75, 0.6M NaCl, and 1% glycerol. Approximately 10 µl to 40 µl of the diluted protein was used for the PEGylation reaction. The Maleimido-PEG reagent described in section F.1 was diluted in a series of 2-fold dilutions using 10 µl transfers of solution containing approximately 1 µl Maleimido-PEG in a 10 µl volume of buffer composed of 20 mM Tris pH 7.4, 0.1M NaCl, and 0.01% Tween. The ratio of the Maleimido-PEG to protein may be varied according to the preferred level of PEGylation of the protein desired. Up to 20-fold excess of Maleimido-PEG to protein still provided for specific reaction of the reagent with cysteine residues of the protein.

The protein and Maleimido-PEG were incubated for one hour at room temperature, although this reaction may be performed at 4° C. for longer periods of time. A sample of the reacted mixture may be analyzed by SDS-PAGE to determine the minimal amount of Maleimido-PEG reagent needed for complete coupling.

Alternatively, the protein was PEGylated during the protein refolding step following expression of the protein in, for example, E. coli as described in D.3. Bacteria transformed with a construct for expression of PN-1 or a PN-1 variant were collected from the culture by centrifugation, resuspended in 10 mM TRIS, pH 8, 1 mM EDTA, and disrupted by high pressure homogenization as described in D.3. Inclusion bodies were collected by centrifugation and washed with 1M NaCl, 0.05% triethylamine. The inclusion bodies were then resuspended in a protein refolding solution of 6M guanidine and the Maleimido-PEG reagent described above added to the solution. The concentration of Maleimido-PEG may be varied according to the preferred level of PEGylation of the protein.

The protein, 6M guanidine refolding solution, and Maleimido-PEG mixture was incubated for one hour at room temperature, although this reaction may be performed at 4° C. for longer periods of time. A sample of the reacted mixture may be analyzed by SDS-PAGE to determine the minimal amount of Maleimido-PEG reagent needed for complete coupling. The PEGylated, refolded PN-1 variant was purified by capture on Fasts sepharose and eluted with 0.6M NaCl, diluted to 0.25M NaCl and passed over FastQ sepharose to remove endotoxin and recaptured on FastS sepharose and eluted with 0.6M NaCl or a gradient of 0.25 to 1M NaCl.

The reactions described above may be used to determine the proper ratio of Maleimido-PEG to protein, and then scaled up to produce commercially acceptable amounts of PEGylated protein.

F.3 Preparation of (Maleimido)$_2$-PEG Reagent (Maleimido)$_2$-PEG is prepared by mixing the following:
1) polyethylene bis[amine]
2) 20 µmol γ-maleimidobutyric acid-N-hydroxy succinimide ester (GMBS)
3) 2 ml 100 mM Caps buffer, pH 10.0

The amount of the components above (particularly 1) and 2)) and the volume indicated may be varied. For example, it is permissible that the difference in the ratio of 10 and 2) can vary by up to 10 to 100 fold, although an excess of GMBS to 1) above is preferred, normally about a 2-fold excess. While various buffers may be substituted for the Caps buffer, it is important that Tris buffers are not used in this mixture, as Tris buffers will quench the reaction. The pH of the buffer used may vary considerably, although buffers having a pH of 10.0 are preferable over buffers having a pH of 8.0. In addition, the mixture above may contain up to 50% DMSO as a cosolvent. It is particularly important that the reaction mixture does not contain a reducing agent such as dithiothreitol (DTT) or β-mercaptoethanol (βME).

The mixture is incubated at 37° C. for 30 minutes, although the reaction temperature may be as low as 4° C. and the reaction time may be extended for up to one hour or more. After incubation, 12 mg of Tris free base or ethanolamine is added to the mixture to quench the NH$_3$ moiety. This quenching step may be omitted.

The reacted mixture is purified by elution through a PD-10 column (G-25) (BioRad) equilibrated with 20 mM Tris (pH 7.4), 100 mM NaCl, and 0.1% Tween. The eluant is collected in 0.5 ml fractions and production of (Maleimido)$_2$-PEG is assayed by precipitation with 50% TCA. The resulting (Maleimido)$_2$-PEG (Mal-PEG) reagent is then used in to modify a selected protein by attachment of PEG to a cysteine residue(s).

F.4 Reaction of (Maleimido)$_2$-PEG with Protein

Prior to reaction of the protein with the (Maleimido)$_2$-PEG reagent, the purified protein (e.g. a PN-1 mutant containing a cysteine residue at position 99) is diluted to a concentration of about 200 µg/ml to 1 mg/ml in any suitable buffer which does not contain DTT or βME. Normally, the buffer is composed of 20 mM PIPES pH 6.75, 0.6M NaCl, and 1% glycerol. Approximately 10 µl to 40 µl of the diluted protein is used for the PEGylation reaction. The (Maleimido)$_2$-PEG reagent described in section F.1 is diluted in a series of 2-fold dilutions using 10 µl transfers of solution containing approximately 1 µl (Maleimido)$_2$-PEG in a 10 µl volume of buffer composed of 20 mM Tris pH 7.4, 0.1M NaCl, and 0.01% Tween. The ratio of the (Maleimido)$_2$-PEG to protein may be varied according to the preferred level of PEGylation of the protein desired.

The protein and (Maleimido)$_2$-PEG are incubated for one hour at room temperature, although this reaction may be performed at 4° C. for longer periods of time. A sample of the reacted mixture may be analyzed by SDS-PAGE to determine the minimal amount of (Maleimido)$_2$-PEG reagent needed for complete coupling.

Alternatively, the protein was PEGylated during the protein refolding step following expression of the protein in, for example, E. coli as described in D.3. Bacteria transformed with a construct for expression of PN-1 or a PN-1 variant were collected from the culture by centrifugation, resuspended in 10 mM TRIS, pH 8, 1 mM EDTA, and disrupted by high pressure homogenization as described in D.3. Inclusion bodies were collected by centrifugation and washed with 1M NaCl, 0.05% triethylamine. The inclusion bodies were then resuspended in a protein refolding solution of 6M guanidine and the (Maleimido)$_2$-PEG reagent described above added to the solution. The concentration of (Maleimido)$_2$-PEG may be varied according to the preferred level of PEGylation of the protein.

The protein, 6M guanidine refolding solution, and (Maleimido)$_2$-PEG mixture was incubated for one hour at room temperature, although this reaction may be performed at 4° C. for longer periods of time. A sample of the reacted mixture may be analyzed by SDS-PAGE to determine the minimal amount of (Maleimido)$_2$-PEG reagent needed for complete coupling. The PEGylated, refolded PN-1 variant was purified by capture on FastS sepharose and eluted with 0.6M NaCl, diluted to 0.25M NaCl and passed over FastQ sepharose to remove endotoxin and recaptured on FastS sepharose and eluted with 0.6M NaCl or a gradient of 0.25 to 1M NaCl.

Alternatively, and particularly where a heterodimeric protein crosslinked by Maleimido-PEG is desired, a first protein is reacted with an excess of (Maleimido)$_2$-PEG reagent and the reaction driven to completion to yield a first protein-Maleimido-PEG Maleimido compound, i.e. a protein having an exposed an reactive Maleimido functional group. This project was at least nominally purified and reacted with either additional protein identical to the first protein or proteins different from the first protein linked to the Maleimido PEG group. The reaction is again driven to completion to complete the final crosslinking step to yield a protein-Maleimido-PEG-Maleimido-protein or protein-Maleimido-PEG-Maleimido-protein' compound.

The reactions described above may be used to determine the proper ratio of (Maleimido)$_2$-PEG to protein, and then scaled up to produce commercially acceptable amounts of PEGylated dimeric or multimeric proteins.

EXAMPLE G

Generation of Cysteine-PEGylated PN-1 Variants

G.1 Selection of amino acid residues of PN-1 for substitution by cysteine

PN-1α and PN-1β contain N-glycosylation sites at amino acid residue positions 99 and 140. Therefore, these sites were selected for site-directed mutagenesis to replace the asparagine at one or both of these positions with cysteine.

Three sites in PN-1 were selected for replacement with cysteine on the basis of the presence of glycosylated residues at a corresponding site in a protein homologous to PN-1. Amino acid residue D192 was selected for replacement with cysteine since the proteins angiotensin and Rab ORF1, each which are homologous to PN-1, are N-glycosylated at the amino acids corresponding to this residue in PN-1. Amino acid residue E230 was selected for replacement with cysteine since baboon $\alpha_1$-antitrypsin ($\alpha_1$-AT), which is homologous to PN-1, is glycosylated at the amino acid residue corresponding to this position in PN-1. Amino acid residue H252 was selected for replacement with cysteine since $\alpha_2$-antiplasmin ($\alpha_2$-AP), another protein homologous to PN-1, is glycosylated at the corresponding residue.

Other amino acid residues were selected for replacement with cysteine on the basis of the position of the amino acid within the three-dimensional structure of PN-1 as determined by X-ray crystallography (FIG. 3). The approximate position of the amino acid residues selected for cysteine substitution are indicated by their corresponding amino acid residue number. The particular amino acid residues identified for mutagenesis in the present example were selected on the basis of the apparent solvent-accessibility of the amino acid and the apparently few number of interactions with other amino acids in the protein.

G.2 Site-directed Mutation of PN-1 to Cysteine

The mutations selected above were generated in PN-1α using site-directed mutagenesis as described in section D.2. Although PN-1α was employed in these experiments, the same mutations in PN-1β are likely to provide the same effects as all the mutations were introduced into the region of amino acid sequence identity between these nearly identical proteins. Briefly, DNA encoding PN-1 was inserted into the plasmid pT7PN1, which has an f1 ori for the production of single-stranded DNA. This plasmid was then transformed into the *E. coli* strain CJ236 for the production of ssDNA to be used as a template for site-directed mutagenesis according to the method of Kunkel (Kunkel, T. A. (1988) in Nucleic Acids and Molecular Biology (Eckstein, F., Lilley, D. M. J. Eds.) Vol. 2, p. 124, Springer-Verlag, Berlin and Heidelberg).

The oligonucleotides used to generate specific mutations within the PN-1 coding region are as follows:

```
N140C  AAT GCA TGG GTT AAA AAC GAA ACC AGG GAT
       AAT GCA TGG GTT AAC TGC GAA ACC AGG GAT
                       HpaI

N99C   GCC GTG TTT GTT AAG AAT GCC TCT GAA ATT
       GCC GTG TTT GTT AAC TGC GCC TCT GAA ATC
                       HpaI

P28C   GTG AAG TCG AGG CCT CAT GAC AAC ATC GTG ATC
       GTG AAG TCG AGG TGC CAT GAC AAC ATC GTG ATC

G52C   CTG GGG GCG GAC TGC AGG ACC AAG AAG
                       PstI

N85C   GTC TCC AAG AAG AAT AAA GAC ATT GTG ACA GTG GCT
       GTC TCC AAG AAG TGC AAA GAT ATC GTG ACA GTG GCT
                              EcoRV

Q116C  AAA GAT GTG TTC CAG TGT GAG GTC CGG
       AAA GAT GTG TTC TGC AGT GAG GTC CGG
                       PstI

N304C  TCA TCA AAG GCA AAT TTT GCA AAA ATA ACA
       TCA TCA AAG GCA TGC TTT GCA AAA ATA ACA
                       SphI

S1C    GAT ATA CAT ATG TCC CAC TTC AAT CCT CTG TCT CTC GAG
       GAT ATA CAT ATG TGC CAC TTC AAT CCC TTA AGT CTC GAG
                                              AflII

GAA CTA GGC
       GAA CTA GGC

R63C   AAG AAG CAG CTC GCC ATG GTG ATG AGA TAC GGC GTA AAT
       AAG AAG CAG CTC GCA ATG GTG ATG TGC TAC GGC GTA AAT
                       NcoI destroyed E125C  GTC CGG AAT GTG AAC TTT GAG GAT CCA GCC TCT
       GTC CGG AAT GTT AAC TTT TGC GAT CCA GCC TCT
                       HpaI D147C  AGG GAT ATG ATT GAC AAT CTG CTG TCC CCA GAT CTT ATT
       AGG GAT ATG ATT TGC AAT CTC TTA AGC CCA GAT CTT ATT
                                   AflII D192C  TTC GTG GCA GCA GAC GGG AAA TCC TAT
       TTC GTG GCA GCA TGC GGG AAA TCC TAT
                       SphI E230C  CCC TAC CAC GGG GAA AGC ATC AGC ATG
       CCC TAC CAC GGC TGC AGC ATC AGC ATG
                       PstI
```

```
-continued
H252C  GCC  ATC  ATC  CCA  CAC  ATC  AGC  ACC  AAG  ACC  ATA  GAC
       GCC  ATC  ATC  CCA  TGT  ATC  AGT  ACT  AAG  ACC  ATA  GAC
                          ‾‾‾       ‾‾‾‾‾‾‾
                                ScaI S263C  ACC  ATA  GAC  AGC  TGG  ATG  AGC  ATG  GTC
       ACC  ATA  GAC  AGT  TGG  ATG  TGC  ATC  ATG  GTC
                      ‾‾C            ‾‾‾
                  PvuII destroyed P267C  AGC  ATC  ATG  GTC  CCC  AAG  AGG  GTG  CAG
       AGC  ATC  ATG  GTC  TGC  AAA  CGC  GTG  CAG
                           ‾‾‾  ‾‾‾
                                AflIII D284C  GCT  GTA  GCA  CAA  ACA  GAT  TTG  AAG  GAG  CCG  CTG
       GCT  GTA  GCA  CAA  ACA  TGT  TTA  AAG  GAG  CCG  CTG
                                ‾‾‾  ‾‾‾
                                DraI
```

The mutants are named according to the single-letter code for the amino acid residue in the native protein, the number of the position of that amino acid within the amino acid sequence of PN-1, and the single-letter code for cysteine (C), the amino acid residue substituted at that site. For example, the mutant S1C produces a PN-1 protein which has the serine at position 1 replaced by cysteine. The top sequence for each mutant above indicates the wild type PN-1 sequence, while the sequence below indicates the mutation introduced in the coding sequence of the mutant. The nucleotides in bold are changed relative to wild type. The codon which is double-underlined is the newly-introduced codon for cysteine. The underlined sequences in the mutated DNA sequence indicate a restriction enzyme site which is introduced into or removed from the nucleotide sequence of the mutant. Introduction of the desired mutation was confirmed by restriction enzyme analysis.

Mutant PN-1 proteins containing multiple cysteine-substituted residues were generated by introduction of a first cysteine mutation by site-directed mutagenesis as described. After confirmation of the insertion of the first cysteine mutation by restriction enzyme analysis, the DNA was subjected to a second round of site-directed mutagenesis using a different oligonucleotide. For example, the double cysteine mutant N99C;N140C was generated by site-directed mutagenesis with the N99C oligonucleotide and confirmation of the presence of the newly introduced HpaI site in the coding sequence. The N99C mutant DNA was then subjected to a second round of site-directed mutagenesis with the N140C oligonucleotide. Table G.5A below lists the single and multiple site mutants generated using these techniques and the oligonucleotides described above.

DNA encoding the mutant PN-1 proteins were expressed and the expressed proteins purified as described in section D.3.

G.3 Reaction of PN-1 and PN-1 Mutants with Maleimido-PEG Reagent

After purification of PN-1 and the PN-1 mutants described above, each protein was reacted with the Maleimido-PEG reagent described in F.1 according to the general protocol of F.2. For example, the mutant N99C;N140C was cysteine-PEGylated using one of the following two protocols.

G.3A PEGylation of PN-1 and PN-1 Variants After Refolding

Purified N99C;N140C protein was diluted to a concentration of about 200 µg/ml in 20 mM PIPES pH 6.75, 0.6M NaCl, 1% glycerol. Approximately 40 µl of the diluted protein (0.25 nmol) was used for the PEGylation reaction. The Maleimido-PEG reagent described in section F.1 was diluted in a series of 2-fold dilutions using 10 µl transfers starting from approximately 2 µl Maleimido-PEG in a 10 µl volume of buffer composed of 20 mM Tris pH 7.4, 0.1M NaCl, and 0.01% Tween. This reaction contained a two-fold excess of the Maleimido-PEG reagent over that required for PEGylation of the number of cysteine sites in the PN-1.

The N99C;N140C protein and maleimido-PEG mixtures were incubated for one hour at room temperature. A sample of each of the reacted mixtures was analyzed by SDS-PAGE. Analysis of this gel revealed that the band migrating at the relative molecular weight of unmodified N99C;N140C PN-1 disappeared as the ratio of Maleimido-PEG to protein increased. Accordingly, as the amount of unmodified N99C;N140C PN-1 in the sample disappeared with increasing Maleimido-PEG concentrations, distinct bands migrating at molecular weights of increasing intervals of approximately 5,000 MW appeared. Thus, reaction of the PN-1 variant produced distinct cysteine-PEGylated proteins containing increasing numbers of PEG units per protein molecule, up to 2 PEG per PN-1 molecule, the maximum number of cysteines available in the N99C;N140C PN-1 variant.

G.3B PEGylation of PN-1 and PN-1 Variants During Refolding

Inclusion bodies from E. coli transformed with DNA encoding the PN-1 variant N99C;N140C were collected by centrifugation and washed with 1M NaCl, 0.05% triethylamine. The inclusion bodies were then resuspended in a protein refolding solution of 6M guanidine. The Maleimido-PEG reagent described in section F.1 was diluted in a series of 2-fold dilutions using 10 µl transfers starting from approximately 2 µl Maleimido-PEG in a 10 µl volume of buffer composed of 20 mM Tris pH 7.4, 0.1M NaCl, and 0.01% Tween. This reaction contained a two-fold excess of the Maleimido-PEG reagent over that required for PEGylation of the number of cysteine sites in the PN-1 variant. The protein, 6M guanidine, and maleimido-PEG mixtures were incubated for one hour at room temperature.

G.3C Characterization of PEGylated PN-1 and PN-1 Variants

Distinct bands representing proteins increasing in relative molecular weight by 5,000 MW intervals is evidence of the specificity of the Maleimido-PEG reaction for attachment of PEG to cysteine residues. If the reaction had resulted in PEGylation of residues other than cysteine, a smear of proteins would appear on the gel, indicating the presence of proteins containing an infinite number of PEG moieties.

Figure 4:
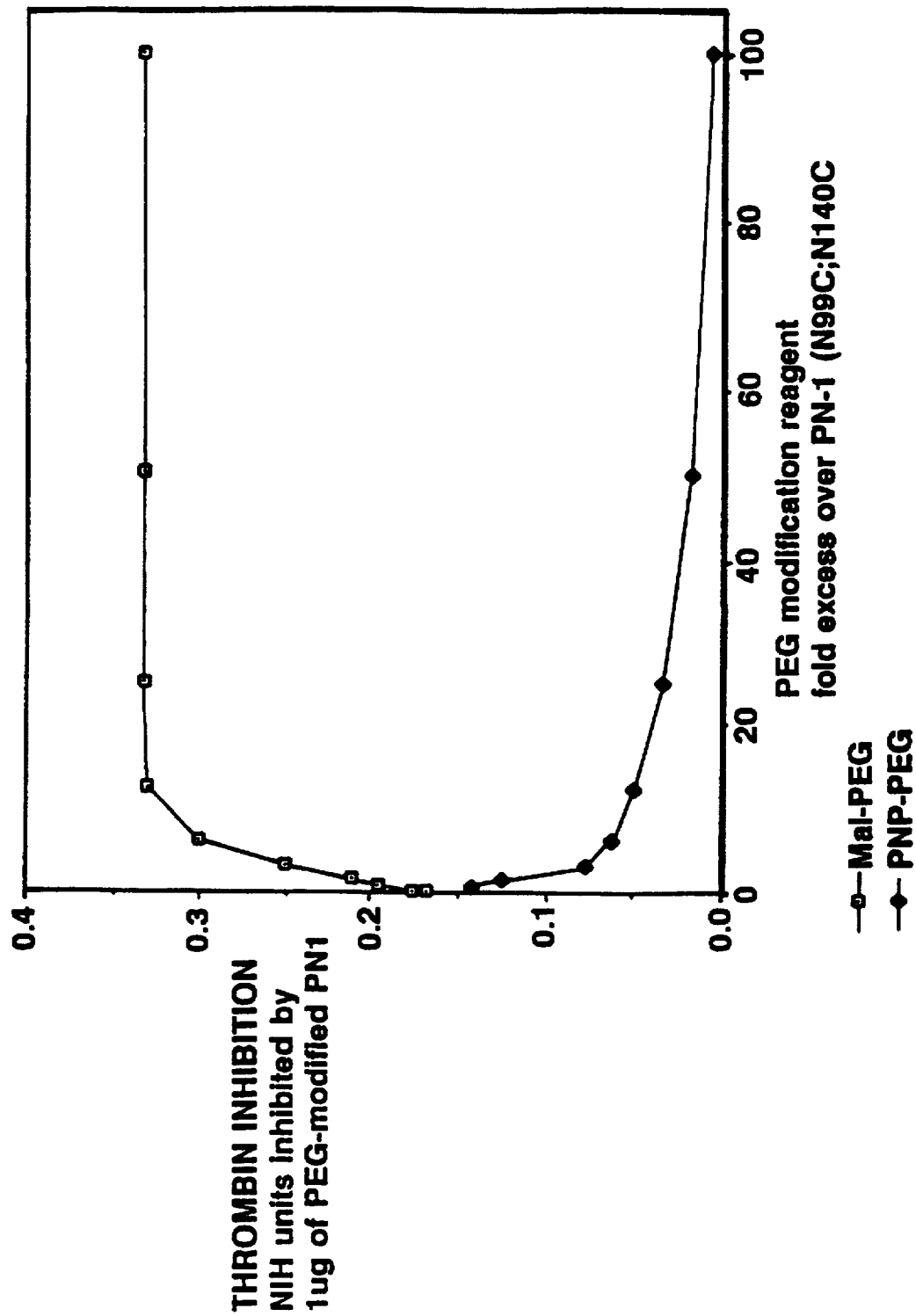
FIG. 4 is a graph which shows the activity of samples of reaction mixtures containing cysteine-PEGylated PN-1 variants (N99C;N140C) produced by the method of the invention (open squares) and the activity of samples of reaction mixtures containing a PEGylated PN-1 variant (N99C;N140C) produced by a conventional method (closed diamonds).

A sample of the cysteine-PEGylated protein which was reacted at a ratio of 3:1 Maleimido-PEG to protein was tested for activity using the assay described in D.4. This sample, which primarily contains cysteine-PEGylated protein, retained at least 100% of the activity of unmodified PN-1. The specific activity of the PEGylated proteins increased with an increasing amount of the Maleimido-PEG reagent present in the reaction mixture (FIG. 4). These data suggest that an increase in activity is often found upon increasing PEG modification, which may result from the increased solubility and/or activity of PEGylated PN-1.

G.4 Generation of PEGylated PN-1 Mutant Using Conventional Method (Comparative Example)

In order to compare the results obtained above with the PEGylation methods known in the art, the N99C;N140C PN-1 variant was PEGylated using a method similar to that described by Zalipsky in U.S. Pat. No. 5,122,614, with the substitution of a paranitrophenol carbonate of PEG for the N-succinimide carbonate of PEG used by Zalipsky as the activated carbonate. The protocol used was otherwise identical. Ratios ranging from 1:1 to 100:1 of activated PEG to PN-1 mutant (N99C;N140C) were used in the reactions.

A sample of each of the reacted mixtures containing dilutions of the PEGylation reagent was analyzed by SDS-PAGE. Analysis of this gel revealed that the amount of protein migrating at the molecular weight of the unmodified PN-1 variant decreased with increasing concentrations of the PEGylation reagent of Zalipsky used in the reaction. However, in contrast to the distinct bands generated using the method of the invention, a smear of proteins of various, increasing molecular weights appeared as the unmodified protein disappeared. The PEGylated proteins produced by the conventional method contained various numbers of PEG moieties per protein molecule, suggesting that attachment of PEG was random and that any number of lysine residues to various positions were modified.

The sample which contained various levels of PEG modification were tested for activity in the assay described in D.4. The data show that as the amount of the Maleimido-PEG reagent present in Maleimido-PEG/protein reaction mixture increased, the specific activity of the protein decreased (FIG. 4). This suggests that increasing levels of PEG modification using the conventional method result in a decrease in the activity of the protein.

G.5 Activity of Cysteine-PEGylated PN-1 and Cysteine-PEGylated PN-1 Mutants Containing Added Cysteines The specific PN-1 mutants and cysteine-PEGylated mutants generated are shown in Table G.5A. Each of the PN-1 site-directed mutant proteins, as well as wild type PN-1, were modified by cysteine-PEGylation using the protocol described in F.2. The activity of wild type PN-1, each of the PN-1 site-directed mutants, and the cysteine-PEGylated wild type and mutant proteins was determined using the assay described in D.4.

TABLE G.5A

| | BEFORE PEG MODIFICATION | | AFTER PEG MODIFICATION | | |
|---|---|---|---|---|---|
| MUTANT | SPECIFIC ACTIVITY[1] | REL TO WT[2] | ACTIV- ITY | REL TO ACTIVITY BEFORE PEG[3] | REL TO WT[2] |
| WT | 0.50 | 1 | 0.017 | 0.03 | |
| N99C | 0.20 | 0.40 | 0.50 | 2.5 | 1.0 |
| N140C | 0.30 | 0.60 | 0.60 | 2.0 | 1.2 |
| N99C; N140C | 0.20 | 0.40 | 0.40 | 2 | 0.80 |
| S1C[5] | 0.10 | 0.20 | 0.25 | 2.5 | 0.50 |
| G52C[5] | 0.024 | 0.048 | 0.05 | 2.1 | 0.1 |
| R63C[5] | 0.050 | 0.10 | 0.125 | 2.5 | 0.25 |
| N85C[5] | 0.033 | 0.066 | 0.040 | 1.2 | 0.080 |
| E125C[5] | 0.095 | 0.19 | 0.15 | 1.57 | 0.3 |
| D147C[5] | 0.063 | 0.125 | 0.125 | 2 | 0.25 |
| D192C[5] | 0.045 | 0.091 | 0.91 | 2 | 0.18 |

TABLE G.5A-continued

| | BEFORE PEG MODIFICATION | | AFTER PEG MODIFICATION | | |
|---|---|---|---|---|---|
| MUTANT | SPECIFIC ACTIVITY[1] | REL TO WT[2] | ACTIV- ITY | REL TO ACTIVITY BEFORE PEG[3] | REL TO WT[2] |
| E230C[5] | 0.071 | 0.14 | 0.20 | 2.8 | 0.40 |
| H252C[5] | 0.10 | 0.20 | 0.25 | 2.5 | 0.50 |
| H252C[5] | 0.10 | 0.20 | 0.25 | 2.5 | 0.50 |
| S263C[5] | 0.05 | 0.1 | 0.093 | 1.86 | 0.19 |
| N304C[5] | 0.056 | 0.11 | 0.17 | 3 | 0.33 |
| C117S; C131S; C209S | 0.050 | | 0.50 | | |

[1]Sp.Act is NIH units of thrombin inhibited per μg PN-1 (variant).
[2]Activity relative to wild type is calculated by dividing the activity of wild type PN-1 by the activity of the mutant.
[3]Activity of cysteine-PEGylated protein relative to activity of this protein before PEGylation is calculated by dividing the activity of the mutant before PEGylation by the activity of the mutant after PEGylation.
[4]Activity of cysteine-PEGylated PN-1 is variable as modification of the naturally occurring Cys 209 inhibits activity.
[5]These mutants are in the N99C;N140C mutant background (i.e. these mutants contain three amino acids substituted with cysteine).
[6]Protein PEGylated during refolding in 6 M guanidine.

The mutations described here for PN-1 can be introduced into any serpin with the expectation of substantially similar effects due to the homology between the members of the serpin protein family.

G.6 Test for Half-Life of Cysteine-PEGylated PN-1 and PN-1 Mutants

The circulating half-life of any protein can be measured by standard methods well known in the art. For example, radioactive PEG-modified protein is injected into a mouse, rat, or rabbit. At various times, blood is withdrawn and the amount of protein remaining in circulation is determined by scintillation counting. Alternatively, PEG-modified PN-1 is injected into a mouse, rat, or rabbit. At various times, blood is withdrawn and urokinase inhibitory activity is measured. In some cases, the amount of protein remaining in circulation can be measured with antibody reaction as in an ELISA or sandwich ELISA.

G.7 In Vivo Half-Life of Cysteine-PEGylated PN-1 Variant

The PN-1 variant N99C;N140C was PEGylated by reaction with the Maleimido-PEG reagent as described above in section G.2. Small scale reactions were first performed to determine the excess of Maleimido-PEG reagent required to drive the reaction to completion, i.e., to PEGylate both the N99C and N140C sites of the protein. The final PEGylation reaction contained about a 3-fold excess of Maleimido-PEG over the amount of N99C;N140C protein in the reaction mixture. Cysteine-PEGylated protein was purified by ion exchange chromatography as described in Section D3 above with an additional final Mono-S ion exchange step. The bis-modified, cysteine-PEGylated N99C;140C protein and unmodified N99C;N140C protein were resuspended in 50 mM PIPES pH 6.7, 150 mM NaCl, 10% glycerol.

The serum half-life of the PEGylated N99C;N140C variant was compared to the half-life of the unmodified N99C;N140C variant by injecting a 0.3 ml of a 3 mg/ml solution containing either the cysteine-PEGylated N99C;N140C or unmodified N99C;N140C into the tail vein of 200 g rats. At 2 min, 10 min, 30 min, 60 min, and 120 min after injection, a 0.5 ml blood sample was collected onto EDTA anticoagulant. The blood samples were centrifuged to separate plasma from blood cells, and the concentration of cysteine-PEGylated N99C;N140C or unmodified N99C;N140C determined by sandwich ELISA as described by Evans et al. (1991) *J. Biol. Chem.* 266:22307–22312, using a rabbit polyclonal antibody. Both unmodified and cysteine-PEGylated N99C;N140C were used as standards in the ELISA assays and gave identical standard curves.

Figure 5:
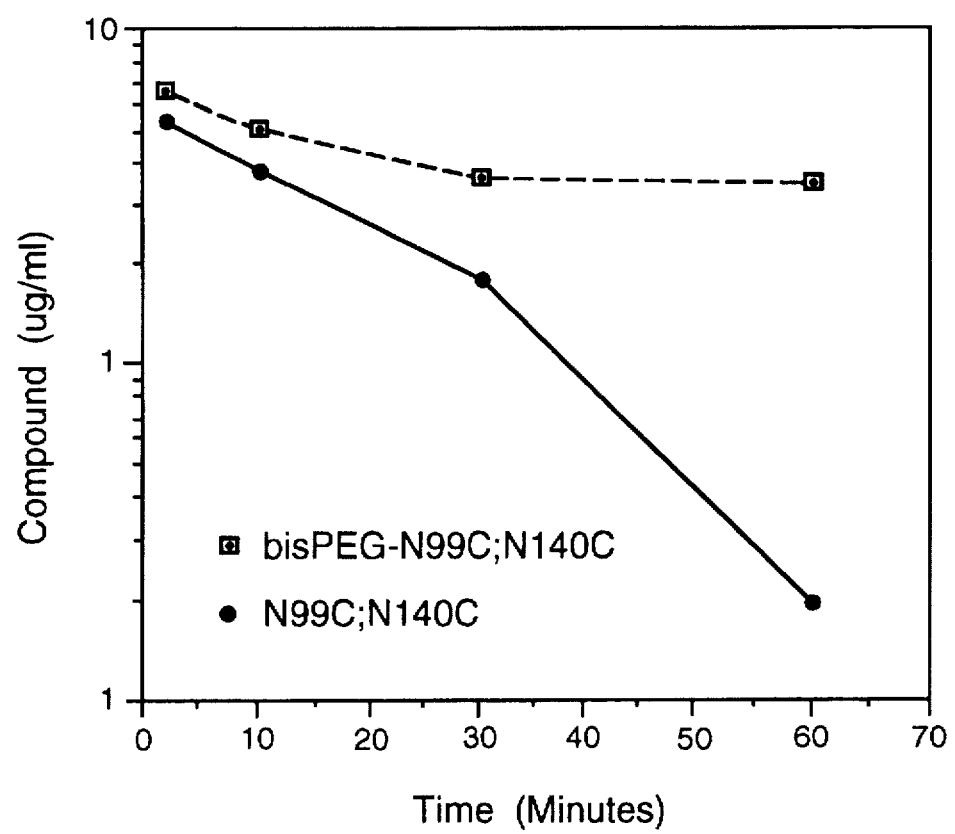
FIG. 5 is a graph showing the serum half-life of unmodified N99C;N140C (diamonds) and cysteine-PEGylated N99C;N140C (squares).

The results of this experiment are shown in FIG. 5. At the 60 min time point, less than 3% of the total administered amount of unmodified N99C;N140C was present in the rat's blood stream. In contrast, 55–60% of the total administered amount of cysteine-PEGylated N99C;N140C was present in the rat's blood stream at 60 min. The $t_{1/2}$ of unmodified N99C;N140C was approximately 10–12 min, while the $t_{1/2}$ of the cysteine-PEGylated N99C;N140C protein was approximately 60–80 min. These data show that cysteine-PEGylation of the N99C;N140C PN-1 variant enhanced the $t_{1/2}$ of the protein by about 6-fold.

G.8 Administration of Cysteine-PEGylated PN-1

Cysteine-PEGylated PN-1 and/or the cysteine-PEGylated PN-1 mutants described above may be used in the treatment of a variety of disease states for which PN-1 is indicated as therapeutically useful. For example, the proteins may be incorporated into a bandage for dressing a wound as described in U.S. Pat. No. 5,196,196, herein incorporated by reference with respect to the use (e.g. dosages and routes of administration) of PN-1 in wound dressings. Alternatively, cysteine-PEGylated PN-1 and/or cysteine-PEGylated PN-1 mutants may be incorporated as the active ingredient(s) in a pharmaceutical compositions for treatment of inflammation and arthritis, as described in U.S. Pat. No. 5,206,017 and U.S. Pat. No. 5,326,562, each incorporated herein by reference with respect to the use (e.g. dosages and routes of administration) of PN-1 in treatment of such conditions.

EXAMPLE H

Generation of Cysteine-PEGylated Erythropoietin (EPO)

H.1 Selection of Amino Acid Residues for Cysteine Substitution

The amino acid sequence of erythropoietin (EPO) is as follows:

*MGVHECPAWLWLLLSLLSLPLGLP VLG*APPRLICDSRVLQRYLLEAKEAE     50

N̲ITTGCAEHCSLNEN̲ITVPDTKVNFYAWKRMEVGQQAVEVWQGLALLSEA     100

VLRGQALLVN̲SSQPWEPLQLHVDKAVSGLRSLTTLLRALGAQKEAISPPD     150

AASAAPLRTITADTFRKLFRVYSNFLRGKLKLYTGEACRTGDR     194

The first 27 amino acids of the protein (italicized) are the EPO signal sequence. The amino acid residues which are in bold and underlined above (N24, N38, and N83) are sites of N-glycosylation in the native EPO protein. These sites are thus selected for replacement with a cysteine residue, which is subsequently modified by PEGylation.

H.2 Site-directed Mutagenesis of EPO

The complete nucleotide sequence which codes for the mature EPO protein is known in the art and available from GenBank. DNA encoding the mature EPO protein is cloned and subjected to site-directed mutagenesis as described in D.2. Oligonucleotides for replacement of residues N24, N38, and N83 with cysteine are as follows:

N24C: GCC AAG GAG GCC GAG TGT ATC ACG ACG GGC

N38C: TGC AGC TTG AAT GAG TGT ATC ACT GTC CCA

N83C: GCC CTG TTG GTC TGC TCT TCC CAG CCG

The residues in bold and underlined indicate the nucleotides which are different relative to the wild type EPO DNA sequence and represent the cysteine codon to be introduced into the EPO amino acid sequence.

The mutant EPO proteins which contain a cysteine residue at N24, N38, N83, or a combination of these site (e.g. double and triple mutants) are generated as described, expressed, and purified using techniques well known in the art.

H.3 Generation of Cysteine-PEGylated EPO and Cysteine-PEGylated EPO Mutants

Purified EPO mutants N24C, N38C, N83C, and mutants containing combinations of these mutations are subjected to cysteine-PEGylation using the protocol described in F.2. Samples of the reacted proteins are analyzed by SDS-PAGE to determine the extent of the PEGylation, as well as the minimum amount of the Maleimido-PEG reagent necessary to produce fully PEGylated protein.

The activity of the cysteine-PEGylated wild type EPO, as well as the cysteine-PEGylated EPO mutants are tested using protocols known in the art.

EXAMPLE I

Generation of Cysteine-PEGylated Human Growth Hormone (hGH)

I.1 Selection of Amino Acid Residues for Cysteine Substitution

The nucleotide sequence, amino acid sequence, and the three-dimensional structure of human growth hormone (hGH) are well known in the art (see, for example, Cunningham and Wells 1989 *Science* 244:1081–1085). In addition, the three-dimensional structure of hGH bound to its receptor is known (De Vos et al. 1992 *Science* 255:306–312). Amino acid residues for replacement with cysteine are selected based upon the solvent-accessibility of the amino acid residue, the proximity of the residue to other amino acid residues with which it may interact, and the distance of the residue from regions of hGH which are known to be important for receptor binding (Cunningham and Wells 1989 *Science* 244:1081–1085).

I.2 Site-directed Mutagenesis of hGH

Oligonucleotides for site-directed mutagenesis are designed so as to introduce a cysteine residue in place of the amino acid residue(s) selected above. Site-directed mutagenesis is performed as described in D.2. The resulting hGH DNA is then inserted into an expression vector, and the resultant protein is expressed in *E. coli* or other suitable host.

The resulting hGH mutant protein is then purified according to methods known in the art.

I.3 Generation of Cysteine-PEGylated hGH

The hGH mutant protein is then subjected to cysteine-PEGylation using the method outlined in F.2. A sample of a reacted mixture of Maleimido-PEG and hGH mutant protein is analyzed by SDS-PAGE to determine the optimal conditions for cysteine-PEGylation (e.g. the minimal amount of the Maleimido-PEG reagent necessary to provide the desired PEGylated hGH mutant protein).

The cysteine-PEGylated hGH protein is then tested for activity by assaying for the ability of the modified protein to bind to purified, truncated hGH receptor, as described in Cunningham and Wells (ibid.).

EXAMPLE J

Generation of Hemoglobin by Cysteine-PEGylation Cross-Linking

Hemoglobin is a tetrameric protein complex composed of two "a" chains and two "b" chains. The amino acid sequences of the "a" and "b" chains of hemoglobin, as well as the tetrameric complex of hemoglobin composed of 2 "a" and 2 "b" chains are well known. Appropriate amino acid residues which are solvent-accessible and minimally contacted with other side chains are selected for site-directed mutagenesis to cysteine. The "a" and "b" chain mutants are then expressed, purified, and allowed to form a tetramer. The mutant tetrameric complex is then reacted with various levels of (Maleimido)$_2$-PEG as described in F.4 above. This reaction can be carried out with very dilute hemoglobin levels to form intramolecular cross-links to stabilize the tetrameric form of hemoglobin, with a minimum number of intermolecular cross-links. Alternatively, the reaction can be carried out a higher with a higher hemoglobin concentration, resulting in higher levels of intermolecular cross-linking to stabilize an aggregate of hemoglobin molecules.

While the present invention has been described with reference to specific proteins, particularly protease nexin-1 variants, and formulations containing such, it should be understood by those skilled in the art that various changes may be made and equivalence may be substituted without departing from the true spirit and scope of the invention. In addition, many modifications may be made to adapt a particular situation, material, excipient, cysteine-PEGylated protein, process, process step or steps to the objective, spirit and scope of the invention. All such modifications are intended to be within the scope of the claims appended hereto.

What is claimed is:

1. A chemically modified protease nexin-1 variant comprised of the amino acid sequence of protease nexin-1, wherein an amino acid residue at a position selected from the group consisting of $P_4$, $P_3$, $P_2$, $P_1$, $P_1'$, $P_2'$, $P_3'$ and $P_4'$ is replaced with a natural amino acid residue which is different from the amino acid residue naturally present at that position, and which sequence includes at least one cysteine residue, wherein the chemical modification comprises the coupling of polyethylene glycol to a cysteine residue of the protein.

2. The chemically modified protease nexin-1 variant protein of claim 1, wherein the variant has a different protease specificity as compared with protease nexin-1 and/or an increased rate association constant with respect to a specific protease as compared with protease nexin-1.

3. A chemically modified protease nexin-1 variant wherein amino acid residues at the active site of protease nexin-1 are replaced with an equivalent number of active site amino acid residues of a serine protease inhibitor other than protease nexin-1, and the amino acid sequence of the variant protein includes at least one cysteine residue, wherein the chemical modification comprises the coupling of polyethylene glycol to a cysteine residue of the protein.

4. The chemically modified variant of claim 3, wherein the serine protease inhibitor is selected from the group consisting of antithrombin III, heparin cofactor II, α-1-protease inhibitor, plasminogen activator inhibitor I, II, & III, α-2-antiplasmin, kallikrein-binding protein, and C1-inhibitor.

5. The chemically modified variant of claim 3, wherein amino acid residues at positions $P_4$, $P_3$, $P_2$, $P_1$, $P_1'$, $P_2'$, $P_3'$ and $P_4'$ of the active site of protease nexin-1 replaced with an amino acid sequence selected from the group consisting of:

| $P_4$ | $P_3$ | $P_2$ | $P_1$ | $P_1'$ | $P_2'$ | $P_3'$ | $P_4'$ |
|---|---|---|---|---|---|---|---|
| Val— | Ser— | Ala— | Arg | Met— | Ala— | Pro— | Glu |
| Met— | Thr— | Gly— | Arg | Thr— | Gly— | His— | Gly |
| Phe— | Thr— | Phe— | Arg | Ser— | Ala— | Arg— | Leu |
| Ile— | Ala— | Gly— | Arg | Ser— | Leu— | Asn— | Pro |
| Ala— | Met— | Ser— | Arg | Met— | Ser— | Leu— | Ser |
| Ser— | Val— | Ala— | Arg | Thr— | Leu— | Leu— | Val |
| Ile— | Leu— | Ser— | Arg | Arg— | Thr— | Ser— | Leu |
| Phe— | Arg— | Ile— | Leu | Ser— | Arg— | Arg— | Thr |
| Ala— | Ile— | Pro— | Met | Ser— | Ile— | Pro— | Pro |
| Glu— | Lys— | Ala— | Trp | Ser— | Lys— | Tyr— | Gln |
| Leu— | Leu— | Ser— | Ala | Leu— | Val— | Glu— | Thr |
| Ile— | Thr— | Leu— | Leu | Ser— | Ala— | Leu— | Val |
| Phe— | Met— | Pro— | Leu | Ser— | Thr— | Glu— | Val |
| Met— | Thr— | Gly— | Arg | Thr— | Gly— | His— | Gly | and the variant protein contains at least one cysteine residue, wherein the chemical modification comprises the coupling of polyethylene glycol to a cysteine residue of the protein.

6. A chemically modified protease nexin-1 variant wherein three or more amino acid residues of the active site of protease nexin-1 are replaced with different amino acid residues which comprise a substrate sequence specific for a given protease and the amino acid sequence of the variant protein includes at least one cysteine residue wherein the chemical modification comprises the coupling of polyethylene glycol to a cysteine residue of the protein.

7. The chemically modified protease nexin-1 variant of claim 6, wherein the given protease is selected from the group consisting of elastase, cathepsin G, C1-esterase, thrombin, kallikrein, Factor Xa, Factor IXa, Factor XXIa, Factor VIIIa, Factor V, Activated Protein C, trypsin, and chymotrypsin.

8. A method of coupling polyethylene glycol to a protease nexin-1 variant comprising the steps of:

determining a site for coupling of polyethylene glycol to a protease nexin-1 variant, wherein said protease nexin-1 variant has an amino acid residue at a position selected from the group consisting of $P_4$, $P_3$, $P_2$, $P_1$, $P_1'$, $P_2'$, $P_3'$ and $P_4'$ replaced with a natural amino acid residue which is different from the amino acid residue naturally present at that position;

introducing a cysteine residue at said site; and coupling polyethylene glycol to the variant at said site wherein the polyethylene glycol is covalently bound to a thio group of a cysteine residue of the variant.

9. A method of coupling polyethylene glycol to a protease nexin-1 variant comprising the steps of:

determining a site for coupling of polyethylene glycol to a protease nexin-1 variant, wherein the protease nexin-1 variant has at least one amino acid residue at the active site of protease nexin-1 replaced with an equivalent number of active site amino acid residues of a serine protease inhibitor other than protease nexin-1;

introducing a cysteine residue at said site; and coupling polyethylene glycol to the variant at said site wherein the polyethylene glycol is covalently bound to a thio group of a cysteine residue of the variant.

10. A method of coupling polyethylene glycol to a protease nexin-1 variant comprising the steps of:

determining a site for coupling of polyethylene glycol to a protease nexin-1 variant, wherein the protease nexin-1 variant has three or more amino acid residues of the active site of protease nexin-1 replaced with different amino acid residues which comprise a substrate sequence specific for a given protease;

introducing a cysteine residue at said site; and coupling polyethylene glycol to the variant at said site wherein the polyethylene glycol is covalently bound to a thio group of a cysteine residue of the variant.

* * * * *

UNITED STATES PATENT AND TRADEMARK OFFICE
CERTIFICATE OF CORRECTION

PATENT NO.   : 5,766,897
DATED        : Jun. 16, 1998
INVENTOR(S)  : Braxton

It is certified that error appears in the above-identified patent and that said Letters Patent is hereby corrected as shown below:

Col. 48, line 12, insert --are-- before "replaced"

Signed and Sealed this

Fourteenth Day of December, 1999

Attest:

Attesting Officer

Q. TODD DICKINSON

Acting Commissioner of Patents and Trademarks